United States Patent
Hill et al.

(10) Patent No.: US 6,234,773 B1
(45) Date of Patent: May 22, 2001

(54) LINEAR PERISTALTIC PUMP WITH RESHAPING FINGERS INTERDIGITATED WITH PUMPING ELEMENTS

(75) Inventors: Roger J. Hill, Richardson; James H. Monti, Jr., Plano; Joseph A. Oliver, Flower Mound, all of TX (US); Gary Lindemann, Cary, NC (US); Harry C. Copp, Carrollton, TX (US)

(73) Assignee: B-Braun Medical, Inc., Bethlehem, PA (US)

( * ) Notice: Subject to any disclaimer, the term of this patent is extended or adjusted under 35 U.S.C. 154(b) by 0 days.

(21) Appl. No.: 09/169,892

(22) Filed: Oct. 12, 1998

Related U.S. Application Data

(63) Continuation-in-part of application No. 08/920,061, filed on Aug. 26, 1997, now Pat. No. 5,888,052, which is a continuation of application No. 08/349,906, filed on Dec. 6, 1994, now Pat. No. 5,660,529.

(51) Int. Cl.$^7$ ............................................. F04B 17/04
(52) U.S. Cl. ........................... 417/474; 417/53; 604/153
(58) Field of Search ............................. 417/53, 474, 476, 417/477.1, 477.9, 478; 604/153

(56) References Cited

U.S. PATENT DOCUMENTS

| | | | |
|---|---|---|---|
| 1,922,196 | 8/1933 | Butler | 103/148 |
| 2,105,200 | 1/1938 | Phelps | 128/230 |
| 2,351,828 | 6/1944 | Marsh | 103/148 |
| 2,412,397 | 12/1946 | Harper | 103/148 |
| 2,420,148 | 5/1947 | Ostergren | 177/351 |
| 2,689,530 | 9/1954 | Harvey | 103/148 |
| 2,770,703 | 11/1956 | Scheurich | 201/63 |

(List continued on next page.)

FOREIGN PATENT DOCUMENTS

| | | | |
|---|---|---|---|
| 32 47 313 A1 | 12/1982 | (DE) | F04B/49/02 |
| 0 283 614 A1 | 2/1987 | (EP) . | |
| 0 446 898 A2 | 3/1991 | (EP) . | |
| 0 426 273 A1 | 8/1991 | (EP) . | |
| 0 499 417 A1 | 7/1992 | (EP) . | |
| 2 225 065 | 5/1990 | (GB) . | |
| 2 238 083 | 5/1991 | (GB) . | |
| 57-27463 | 6/1982 | (JP) . | |
| 58-165868 | 9/1983 | (JP) . | |

OTHER PUBLICATIONS

Mark's Standard Handbook for Mechanical Engineers 10th Edition. McGraw–Hill, Jan. 1996.*
IBM Technical Disclosure Bulletin, vol. 7, No. 11, Apr. 1965, pp. 1034–1035; R.T. Albo.

Primary Examiner—Timothy S. Thorpe
Assistant Examiner—Timothy P Solak
(74) Attorney, Agent, or Firm—Haynes and Boone, LLP; John W. Montgomery

(57) ABSTRACT

A linear peristaltic pump of the type for removable engagement of a portion of a flexible tubing and having a plurality of sequentially actuated pumping elements which act along the engaged portion of the flexible tubing, with the pumping elements reciprocated in a first direction to collapse adjacent segments of the tubing and then in a second direction to release the adjacent segments of the tubing, each pumping element having a flat pumping surface reciprocated in a sequence so that fluid in the flexible tubing is moved along the engaged portion of the tubing. The linear peristaltic pump is provided with a plurality of opposed pairs of pivotable reshaping fingers, with each pair of the reshaping fingers interposed adjacent to one of the pumping elements in sequence along the engaged portion of the flexible tubing. A finger drive and follower mechanism is formed by and engaged between each of the plurality of pairs of reshaping fingers and the adjacent ones of the pumping elements for actuating the reshaping fingers into reshaping engagement with the flexible tubing upon release thereof by the adjacent one of the pumping elements.

9 Claims, 10 Drawing Sheets

U.S. PATENT DOCUMENTS

| | | | |
|---|---|---|---|
| 2,877,714 | 3/1959 | Sorg et al. | 103/149 |
| 2,885,520 | 5/1959 | Giovanni | 201/63 |
| 3,083,647 | 4/1963 | Muller | 103/148 |
| 3,227,091 | 1/1966 | Isreeli et al. | 103/149 |
| 3,233,553 | 2/1966 | Chanton | 417/474 |
| 3,279,388 | 10/1966 | Roudaut | 103/148 |
| 3,314,371 | 4/1967 | Hopkinson | 103/148 |
| 3,433,171 | 3/1969 | Corneil | 103/149 |
| 3,518,033 | 6/1970 | Anderson | 417/478 |
| 3,606,596 | 9/1971 | Edwards | 417/479 |
| 3,609,069 | 9/1971 | Martinelli | 417/474 |
| 3,654,959 | 4/1972 | Kassel | 137/605 |
| 3,778,195 | 12/1973 | Bamberg | 417/474 |
| 3,866,473 | 2/1975 | Teitelbaum et al. | 73/398 |
| 3,981,633 | 9/1976 | Wall | 417/474 |
| 4,039,269 | 8/1977 | Pickering | 417/475 |
| 4,061,142 | 12/1977 | Tuttle | 128/214 |
| 4,137,940 | 2/1979 | Faisandier | 137/486 |
| 4,155,362 | 5/1979 | Jess | 128/214 |
| 4,199,307 | 4/1980 | Jassawalla | 417/474 |
| 4,236,880 | 12/1980 | Archibald | 417/478 |
| 4,273,121 | 6/1981 | Jassawalla | 128/214 |
| 4,277,226 | 7/1981 | Archibald | 417/38 |
| 4,302,164 * | 11/1981 | Manella | 417/474 |
| 4,303,376 | 12/1981 | Siekmann | 417/360 |
| 4,306,460 | 12/1981 | Sakurai et al. | 73/721 |
| 4,309,908 | 1/1982 | Rapp et al. | 73/720 |
| 4,322,201 | 3/1982 | Archibald | 417/279 |
| 4,345,476 | 8/1982 | Singh | 73/720 |
| 4,346,705 | 8/1982 | Pekkarinen et al. | 128/124 |
| 4,373,525 | 2/1983 | Kobayashi | 128/124 |
| 4,380,236 | 4/1983 | Norton | 604/151 |
| 4,391,600 | 7/1983 | Archibald | 604/153 |
| 4,394,862 | 7/1983 | Shim | 604/67 |
| 4,410,322 | 10/1983 | Archibald | 604/153 |
| 4,443,216 | 4/1984 | Chappell | 604/67 |
| 4,453,931 | 6/1984 | Pastrone | 604/153 |
| 4,468,219 | 8/1984 | George et al. | 604/66 |
| 4,479,797 | 10/1984 | Kobayashi et al. | 604/153 |
| 4,482,347 | 11/1984 | Borsanyi | 604/153 |
| 4,492,538 | 1/1985 | Iwata | 417/477 |
| 4,493,706 | 1/1985 | Borsanyi et al. | 604/153 |
| 4,496,351 | 1/1985 | Hillel et al. | 604/250 |
| 4,519,792 | 5/1985 | Dawe | 604/152 |
| 4,526,574 | 7/1985 | Pekkarinen | 604/52 |
| 4,559,038 | 12/1985 | Berg et al. | 604/153 |
| 4,561,830 | 12/1985 | Bradley | 417/474 |
| 4,563,179 | 1/1986 | Sakai | 604/244 |
| 4,565,542 | 1/1986 | Berg | 604/131 |
| 4,596,550 | 6/1986 | Troutner | 604/5 |
| 4,604,034 | 8/1986 | Wheeldon et al. | 417/18 |
| 4,617,014 | 10/1986 | Cannon et al. | 604/67 |
| 4,650,469 | 3/1987 | Berg et al. | 604/131 |
| 4,653,987 | 3/1987 | Tsuji et al. | 417/360 |
| 4,657,490 | 4/1987 | Abbott | 417/478 |
| 4,690,673 | 9/1987 | Bloomquist | 604/67 |
| 4,728,265 | 3/1988 | Cannon | 417/363 |
| 4,731,057 | 3/1988 | Tanaka et al. | 604/153 |
| 4,735,557 | 4/1988 | Neumüller et al. | 417/477 |
| 4,746,279 * | 5/1988 | Manella | 417/474 |
| 4,781,548 | 11/1988 | Alderson et al. | 417/474 |
| 4,836,752 | 6/1989 | Burkett | 417/12 |
| 4,867,744 | 9/1989 | Borsanyi | 604/153 |
| 4,869,646 | 9/1989 | Gordon et al. | 417/18 |
| 4,893,991 | 1/1990 | Heminway et al. | 417/53 |
| 4,909,710 | 3/1990 | Kaplan et al. | 417/53 |
| 4,952,124 | 8/1990 | Ogami | 417/474 |
| 4,954,046 | 9/1990 | Irvin et al. | 417/53 |
| 4,967,940 | 11/1990 | Blette et al. | 222/214 |
| 5,024,586 | 6/1991 | Meiri | 417/477 |
| 5,034,004 | 7/1991 | Crankshaw | 604/154 |
| 5,055,001 | 10/1991 | Natwick et al. | 417/63 |
| 5,055,013 | 10/1991 | Faeser | 417/474 |
| 5,056,992 | 10/1991 | Simons et al. | 417/474 |
| 5,072,749 | 12/1991 | Ligh | 137/116.5 |
| 5,092,749 | 3/1992 | Meijer | 417/474 |
| 5,098,380 | 3/1992 | Aizawa | 604/67 |
| 5,116,203 | 5/1992 | Natwick et al. | 417/53 |
| 5,151,019 | 9/1992 | Danby et al. | 417/474 |
| 5,152,680 | 10/1992 | Okada | 417/474 |
| 5,158,437 * | 10/1992 | Natwick et al. | 417/53 |
| 5,165,873 | 11/1992 | Meijer | 417/474 |
| 5,165,874 | 11/1992 | Sancoff et al. | 417/474 |
| 5,199,852 | 4/1993 | Danby | 417/26 |
| 5,211,548 | 5/1993 | Okada | 417/474 |
| 5,217,355 | 6/1993 | Hyman et al. | 417/474 |
| 5,219,327 | 6/1993 | Okada | 604/34 |
| 5,279,556 | 1/1994 | Goi et al. | 604/67 |
| 5,302,093 | 4/1994 | Owens et al. | 417/474 |
| 5,318,413 | 6/1994 | Bertoncini | 417/475 |
| 5,320,502 | 6/1994 | Davis | 417/474 |
| 5,320,503 | 6/1994 | Davis | 417/474 |
| 5,322,422 | 6/1994 | Natwick et al. | 417/474 |
| 5,342,180 | 8/1994 | Daoud | 417/412 |
| 5,370,612 | 12/1994 | Maeda et al. | 604/67 |
| 5,499,906 | 3/1996 | O'Leary | 417/53 |
| 5,511,951 | 4/1996 | O'Leary | 417/53 |
| 5,513,957 | 5/1996 | O'Leary | 417/53 |
| 5,531,680 | 7/1996 | Dumas et al. | 604/67 |
| 5,538,405 | 7/1996 | Patno et al. | 417/326 |
| 5,549,460 | 8/1996 | O'Leary | 417/474 |
| 5,584,667 | 12/1996 | Davis | 417/53 |
| 5,660,529 | 8/1997 | Hill | 417/53 |
| 5,827,223 | 10/1998 | Butterfield | 604/65 |
| 5,888,052 | 3/1999 | Hill | 417/53 |

* cited by examiner

LINEAR PERISTALTIC PUMP WITH RESHAPING FINGERS INTERDIGITATED WITH PUMPING ELEMENTS

RELATED APPLICATIONS

This is a continuation-in-part of U.S. application Ser. No. 08/920,061, filed Aug. 26, 1997 now U.S. Pat. No. 5,888,052 which is a continuation of U.S. application Ser. No. 08/349,906, filed Dec. 6, 1994, now U.S. Pat. No. 5,660,529 which are relied upon for priority and incorporated by reference to the full extent permissible by law as if fully set forth herein.

TECHNICAL FIELD OF THE INVENTION

The present invention relates to a linear peristaltic pump for providing adjustable volumetric flow through a flexible, fluid-filled tubing, such as with infusion, of intravenous solutions through a flexible IV tubing. Particularly, the invention relates to a pump having plurality of pumping elements or plungers which operate sequentially and repeatedly along a portion of the flexible fluid carrying tubing to squeeze the fluid therealong with a "milking" type of action. Fluid is forced through the tubing from the entry end to the output end in the direction of the sequential actuation of the pumping elements. The volumetric flow rate is adjusted by changing the rate of sequential and repeated squeezing.

BACKGROUND OF THE INVENTION

Traditionally intravenous infusion has been accomplished using gravity flow systems or drip regulated systems. Modern advances for regulating intravenous infusion have included various types of volumetric pumping systems. In situations where a patient is already established with a gravity-fed or drip-type IV, it often becomes helpful to convert the same system into one with a pump-controlled volumetric flow. For example, an emergency IV can be established in the field by paramedics, and upon arrival at a hospital, a doctor may need to administer medication at a precisely controlled flow rate. The same IV tubing system can then be conveniently adapted for controlled volumetric flow pumping through the use of various types of peristaltic pumps which engage the exterior of the established IV tubing. The typical IV tubing is made of a medical grade polyvinyl chloride (PVC) which has thin walls and is both flexible and resilient. Other more expensive tubing has been proposed to reduce collapsing, but at a cost of about ten times as much as PVC tubing. Alternatively, a combination of types of tubing has been proposed, such as silicon tubing spliced along a length which will be subjected to peristaltic pumping action. Such combination systems can also have a cost significantly greater than PVC (about five to eight times as much), because of the materials, splicing and additional sterilization required. Pumps which act upon the outside of the tubing walls to pump fluid within the tubing at a controlled rate permit the medical practitioners to avoid disturbing existing catheters or needles already established into the patient.

Thus, various types of modern pumps have been used for pumping fluid through an IV tubing, including pumps with a rotating arm, with rollers affixed at both ends of the arm. The rollers are positioned adjacent a curved IV holding channel to engage and roll along a section of tubing placed into the holding channel, thereby advancing a column of liquid there through. As the arm rotates, the rollers alternately engage the tubing, one behind the other, and successive columns of liquid are moved through the tubing. Rotation of the arm continues and repeats the pumping action.

Another type of pump is one which is referred to as a single-plunger peristaltic pump. This type of pump has an entry valve which compresses the tubing shut at an upstream point. A single elongated plunger then squeezes a predetermined length of the tubing along a linear section ahead of the closed entry valve. An outlet valve then compresses the tubing downstream from the elongated plunger after the liquid in the linear section is squeezed out and moved toward the patient. With the outlet valve closed, the entry valve is opened and the elongated plunger is retracted to allow fluid to move back into the linear section between the entry valve and the outlet valve. The entry valve is then closed, and the outlet valve is opened so that compression of the single, elongated plunger can pump more fluid through the tubing.

Another type of pump, which is referred to here as a linear peristaltic pump, uses a series of pumping elements which each engage and sequentially compress a plurality of small segments along an engaged portion of the IV tubing. Each pumping element in sequence at its maximum stroke acts as a seal valve to prevent unwanted reverse flow. Separate inlet and outlet valves are not required in such a linear peristaltic pump. The sequence repeats, and the pumping element reciprocating strokes are typically timed to repeat the milking cycle without interruption. The rate of flow is controlled by changing the rate of reciprocation while the magnitude of the stroke is constant.

With each of the various types of peristaltic pumps described above, the IV tubing is repeatedly collapsed to force the fluid out of the tubing in one direction and then released to allow fluid to reenter from the other direction. After a period of use, the PVC tubing material becomes progressively flattened and permanently deformed such that the walls become creased and the interior volume of the tubing changes over the normal time period of operation. Tubing subject to permanent deformation reduces the pumping efficiency and reduces the accuracy of the pump. To the extent that attempts at reshaping may cause additional crease lines, the risk of premature cracking, tearing or rupture may also be increased, particularly at crease lines. Thus, the tubing must be changed frequently and must be carefully monitored to avoid lost efficiency, inadequate flow, inaccurate and improper volumetric flow or other failure of the system.

SUMMARY OF THE INVENTION

The present invention provides advantages of a linear peristaltic pump and overcomes many of the difficulties which arrive with other types of peristaltic pumps. The use of a linear peristaltic pump with a plurality of sequentially actuated elements does not require separate entry and outlet valves as with the single plunger type of peristaltic pump. The present invention further provides reshaping fingers, which engage a flexible fluid-filled tubing, such as an IV tubing, adjacent to each pumping element contact point, thereby continuously returning the tubing to a constant internal volume and thus maintaining a constant flow rate during operation at a given speed. The time of operation before the tubing becomes permanently deformed is increased. A plurality of pairs of interdigitated reshaping fingers are used and are sequentially actuated transverse to the actuation direction of the pumping elements along the engaged length of the tubing. The interdigitated positioning of the reshaping fingers with the pumping elements advantageously facilitates reshaping of the tubing immediately adjacent each of the compression elements so that reshaping of the tubing is effectively accomplished. Further, the present invention provides pairs of opposed reshaping fingers, each having concave jaws which the shape of a cylindrical arc matching the outside diameter of the flexible tubing. The unique arc shape of the jaws, and particularly a substantial arc of more than about 90°, is made possible by the interdigitation of the fingers with the pumping elements so that reshaping does not interfere with the pumping elements. The result is to round the tubing to its original dimensions without adding additional stress or fatigue and without causing additional potential rupture corners.

According to another aspect of the present invention, a pressure sensor is provided upstream from the pump engagement portion at which the flexible tubing is acted upon by reciprocating pumping elements. A second sensor is provided downstream from the pumping elements and a valve mechanism is provided for closing the flexible tubing downstream from the second pressure sensor. During operation, the tubing will be closed at at least one of the pumping element at any given time so that the upstream pressure can be measured separate from the downstream and the downstream pressure likewise can be measured separate from the upstream pressure. At initialization of the pump, the downstream and upstream sensors are calibrated by closing the downstream valve and disengaging the flexible tubing from compression by the pumping elements. The disengagement is advantageously accomplished by providing a retractable backing plate that is spring-loaded against a face of the pump overlying the pumping plates. The spring force is sufficient to hold the retractable backing plate against the pump face, even when one or two of the pumping elements is compressed against the flexible tubing. At initialization, a backing plate retracting mechanism is actuated and the downstream valve is closed so that the flexible tubing is opened, extending from the upstream sensor to the downstream sensor. Thus, the fluid pressure within the tubing is equalized and the upstream and downstream pressure sensors are calibrated relative to one another.

According to a further aspect of the present invention, the reshaping fingers are pivotably mounted at a position distal from the flexible tubing and finger driving projections are formed on the pumping plates at a position proximal to the flexible tubing. Advantageously the finger drive projections include a first angled surface at a corner of the pumping plate and a second angled surface centrally located on the pumping plate, thereby defining an angled channel into which a rounded boss formed on the proximal end of the reshaping finger is guided into and out of reshaping contact with the flexible tubing upon reciprocation of the pumping plate out of and into compression against the flexible tubing.

BRIEF DESCRIPTION OF THE DRAWINGS

The foregoing objects, advantages, and features, as well as other objects and advantages, will become more apparent with reference to the description and drawings below, in which like numerals represent like elements and in which.

DETAILED DESCRIPTION OF THE PREFERRED EMBODIMENTS

Figure 1:
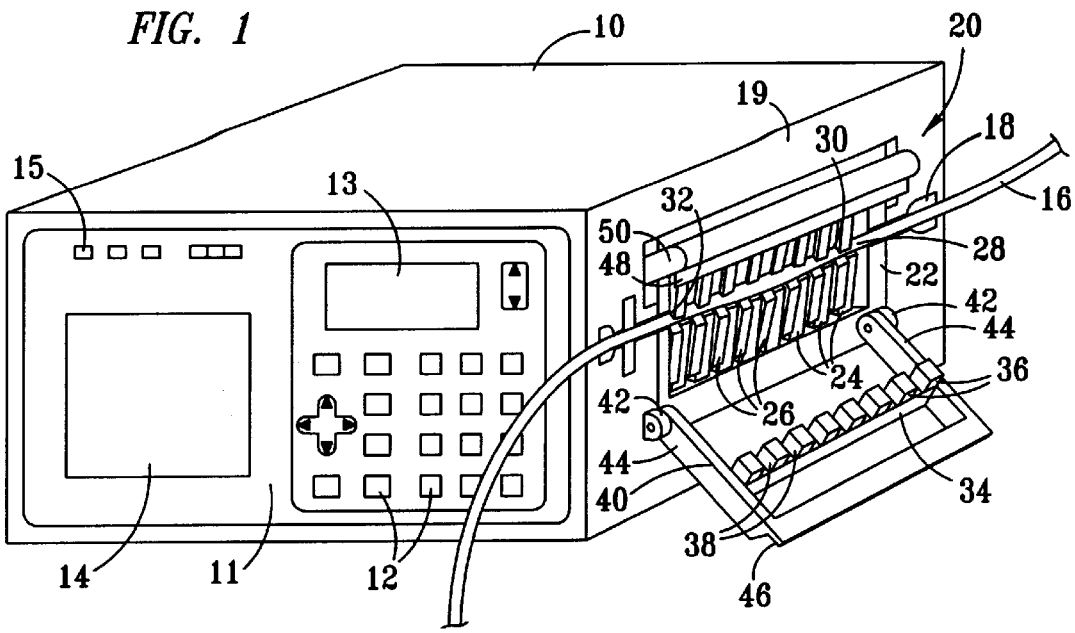
FIG. 1 is a schematic perspective view of one example of an operational linear peristaltic pump, depicting an example of the inventive pumping and reshaping mechanism, shown mounted in the pump at a position for engagement with a flexible tubing according to the present invention.

FIG. 1 depicts a schematic perspective view of an example of one preferred embodiment of a linear peristaltic pump control box 10, having a control panel 11 with control buttons 12, control display 13 and 14 and indicator lights 15. The nature and arrangement of the control panel display buttons and indicators can be as shown in FIG. 1 or in other configurations as may become desirable. The linear peristaltic pump control box is constructed to releasably engage a flexible tubing 16 along an engagement pathway 18, which is conveniently located along one surface 19 of the linear peristaltic pump control box 10. Also, schematically depicted is one preferred embodiment of a pumping element and reshaping finger assembly 20, attached to control box 10 and positioned along the engagement pathway 18 in surface 19 of the control box 10. The pumping element and reshaping finger assembly 20 may advantageously include a housing 22, which housing 22 is preferably constructed for attachment within the pump control box 10 or may be integrally formed as part of the control box 10. The housing typically takes the shape of a box having sidewalls, ends and a bottom, as will be discussed more fully below.

Figure 2:
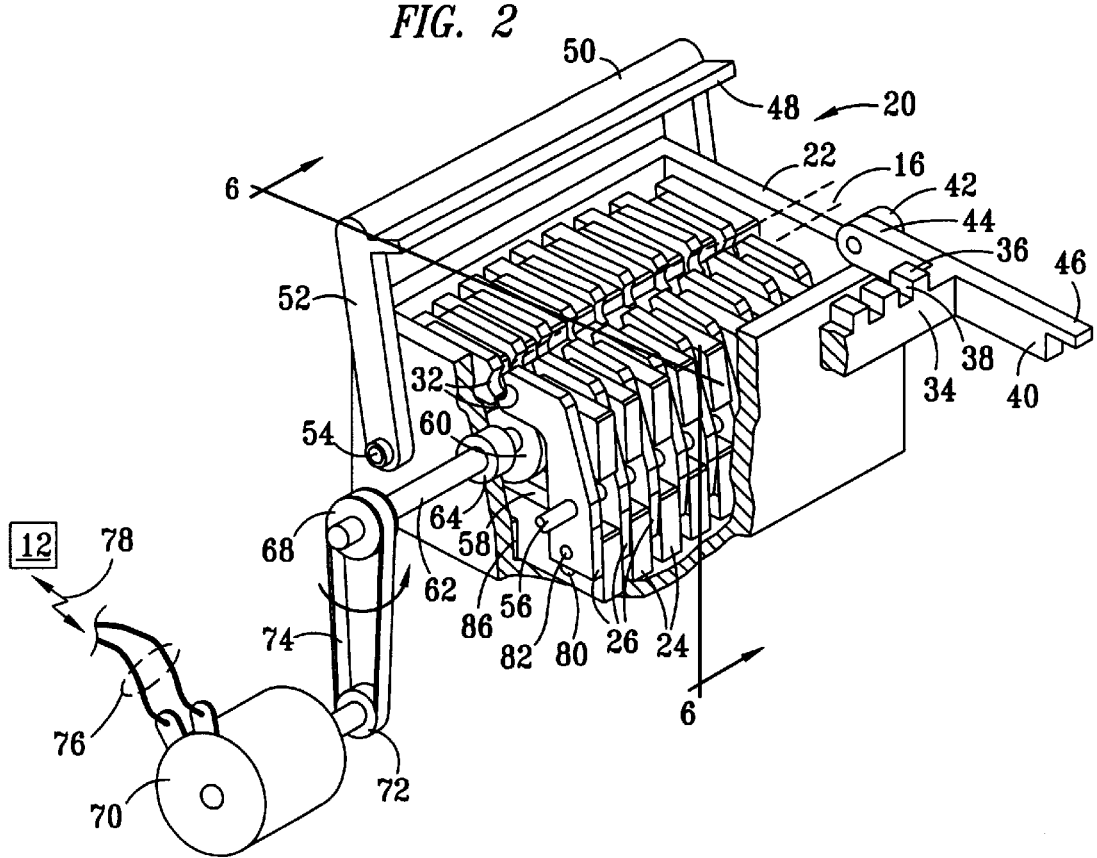
FIG. 2 is a schematic perspective, partial cutaway view of an example of the inventive pumping and reshaping mechanism, including a plurality of pumping elements, which, in this embodiment, are in the form of pumping element plates and with interdigitated reshaping fingers and variable-speed drive motor according to the present invention.

In the preferred embodiment depicted in FIGS. 1 and 2, the pumping element and reshaping finger assembly 20 includes a plurality of pumping elements 24 and a plurality of reshaping fingers 26 which are interdigitated between each of the plurality of pumping elements 24. The pumping elements 24 and the interdigitated reshaping fingers 26 are preferably constructed as flat, pumping plates 24 and flat reshaping fingers 26, respectively. In the embodiment shown, each of the plurality of the pumping element plates 24 has an upper element cutout 30, which allows the flexible tubing 16 to fit thereinto. The cutouts 30 of the pumping elements are aligned to define an engagement channel 28 aligned with engagement pathway 18. Also, the plurality of interdigitated reshaping fingers 26 include pairs of opposed fingers 26i and 26ii, which are aligned in planes between each of the pumping element plates 24. The pairs of opposed interdigitated reshaping fingers 26i and 26ii each have corresponding opposed jaws 32i and 32ii. Each pair of opposed jaws preferably defines a substantially cylindrical opening having a diameter corresponding to the diameter of the flexible tubing 16.

In the preferred embodiment, there is a plurality of pairs of fingers along the engagement length of tubing, and in a particularly preferred embodiment, the number of pairs of fingers corresponds to the number of pumping elements, plus one. The pairs of jaws of the plurality of reshaping finger pairs are pivotably attached so that a plurality of cylindrical shaped openings are defined by the fully actuated jaws which are coaxially aligned with the plurality of pumping element cutouts 30 so that engagement channel 28 results. In the embodiment depicted, there is a backing support bar 34, having a plurality of backing blocks 36 projecting therefrom, with a plurality of gaps 38 between the backing blocks. The backing support bar 34 is attached to provide resistive surfaces against which each pumping element can compress the flexible tubing 16. In the embodiment shown, engagement of the flexible tubing 16, once inserted in channel 28, is accomplished using a backing support bar 34 which pivots from an open or receiving position to a closed resistive support position. Support bar 34 in this embodiment is attached to pivot arms 44, which are pivotably engaged with pivot bosses 42 so that the plurality of backing blocks 36 are attached along support bar 34 so that all of the backing blocks 36 can be pivoted into an adjacent resistive support relationship to each of the pumping element plates 24. The backing blocks 36, according to this embodiment, are thus aligned for partial insertion into the cutouts 30 of the pumping element plates 24. Engagement edges 46 on the engagement bosses 40 can be moved under a locking ledge 48 on a movable locking handle 50 which thereby holds the support bar 34 and backing blocks 36 in position. The plurality of backing blocks 36 securely hold the flexible tubing 16 within the engagement channel 28. The pumping element plates 24 can then be sequentially actuated to compress the flexible tubing against the plurality of backing blocks 36 in a sequential fashion. The gaps 38 allow the reshaping fingers to contact the flexible tubing around an arc without interference from the backing blocks 36 or the support bar 34. With consistent size tubing, the backing blocks can be held rigidly in place. In the preferred embodiment depicted, a small amount of flexibility is provided on the pumping element side to accommodate small variations of tubing size and/or tubing thickness. It will be understood based upon the disclosure herein that flexibility might also be provided as with a spring-loaded support bar or spring-loaded backing blocks (not shown).

Upon reading this disclosure, others may understand that other forms of engagement pathways 18 may be formed without cutouts 30 in the pumping elements. The backing blocks may be rigid or spring-loaded, for example. However, advantageously in such embodiments, gaps or spaces between the backing blocks will facilitate movement of interdigitated reshaping fingers against the tubing, particularly where the fingers have concave jaws.

FIG. 2 is a schematic perspective view with a partial cutaway section of the inventive pumping plate and reshaping finger assembly 20. The locking handle 50 is attached to a pair of latch arms 52, which coaxially pivot about latch pivot axis 54. The latch pivot 54 may conveniently be formed using a rod, a screw, a bolt or other fastener which is attached to the housing. Another fastener rod 56 extends through the plurality of reshaping fingers 26i along one side of the housing. This provides a pivot axis for each of the reshaping fingers 26i on one side of the assembly 20. Either latch pivot 54 or another pivot rod 56ii along the other side of the mechanism assembly 20, as with fastener rod 56, may also be a rod, screw, bolt or other similar fastener which extends through reshaping fingers 26ii toward the opposed side of the assembly 20 to provide a pivot axis for the opposed fingers 26ii of the pairs of interdigitated reshaping fingers 26.

Each of the plurality of pumping element plates 24 is preferably formed with a cam follower opening 58, and each is driven with corresponding pumping element drive cams 60. Upon reading this disclosure, others may become aware of other mechanisms and ways to get cam actuation motion, according to this disclosure. However, in the preferred embodiment shown, each of the drive cams 60 is advantageously a rotary cam 60, and each is secured to a drive shaft 62 so that a rotary camshaft results with a plurality of offset cam lobes. Each drive cam has a maximum eccentricity to drive each pumping element plate an equal distance as each other (i.e., with the same stroke). Thus, each pumping element reciprocates the same distance as each other pumping element. Preferably, all of the cams 60 are mounted to a single drive shaft 62, and all have the same amount of eccentricity; however, the maximum eccentricity of each cam is angularly offset from each adjacent cam a predetermined amount.

The drive shaft 62 extends through housing 22 for rotation as at bearing 64. The drive shaft may be driven in rotation by a motor 70, which is preferably a variable-speed motor. The driving force to the drive shaft 62 may be provided directly from a motor or may be provided through appropriate transmission mechanisms. In the embodiment depicted, a first pulley or gear 68 on drive shaft 62 and a second pulley or sprocket 72 on motor 70 are interconnected as with belt or chain 74. Preferably, the belt or chain 74 and the pulleys or sprocket 68 and 72 are of a type which prevents slippage, such as a chain or a belt and pulley of the type having mating teeth. The variable-speed motor is controlled by a signal 78 responsive to input from control panel 11 as may be input with control buttons 12, which signal is provided to select the speed of motor 70 as through electrical connectors 76. This effectively controls the pumping rate of mechanism 20.

Advantageously, at least one pumping element of the sequence will be in a fully compressed position at all times, so that reverse flow is prevented. In a preferred embodiment, the angular amount of offset, to ensure that at least one pumping element is closing the tubing, can be calculated by dividing 360° by the number of pumping elements, minus one, as in the following equation:

$$\frac{360}{(\text{no. of pumping elements} - 1)} = \text{angular offset for each cam}$$

This amount of angular offset between each cam in a sequence of any predetermined number of pumping elements will ensure that at least one pumping element is in the fully compressed position at any given point in the cam drive shaft rotation. If, for example, the first pumping element 24a, of a series of eight pumping elements 24a, 24b, 24c, 24d, 24e, 24f, 24g and 24h, is in a fully compressed position (i.e., with the tubing in a fully closed condition), then the last pumping element plate 24h of the series will also be in a fully compressed position when the angular spacing is calculated by the above formula, as follows:

$$\frac{360°}{(8-1)} = \frac{360°}{7} = 51.4°$$

At any other cam rotation position, one of the other pumping elements will be fully compressed. In the embodiment depicted, there are eight pumping cams, and each cam is offset angularly around shaft 62 by approximately 51.4° from each next adjacent cam 60a to 60b, 60b to 60c, etc., so that the first and the eighth cams 60h have their maximum eccentricity in the same angular direction with respect to shaft 62. The first cam 60a actuates the pumping element 24a to a fully compressed position, and the eighth cam 60h simultaneously actuates plate 24h to a compressed position and then it moves toward a released or opened position. Each cam, in sequence, actuates a corresponding pumping element so that a column of fluid within the IV tubing 16 is moved from the first pumping element plate 24a, to the next adjacent pumping plate 24b and in sequence along the engaged portion of the IV tubing and out past the eighth pumping element plate 24h.

Figure 3:
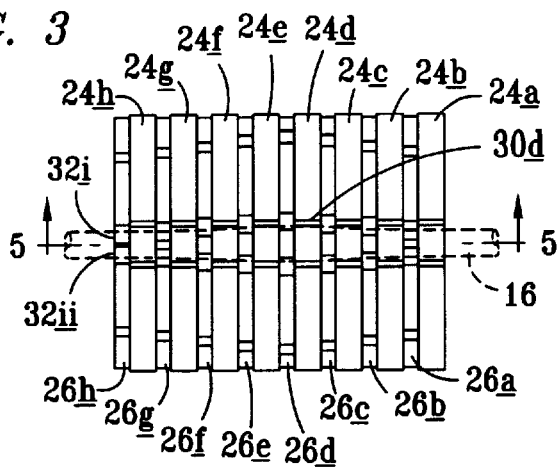
FIG. 3 is a top schematic plan view of a portion of the pumping and reshaping mechanism of FIG. 2 showing a plurality of pumping element plates and interdigitated reshaping fingers according to the present invention.
Figure 5:
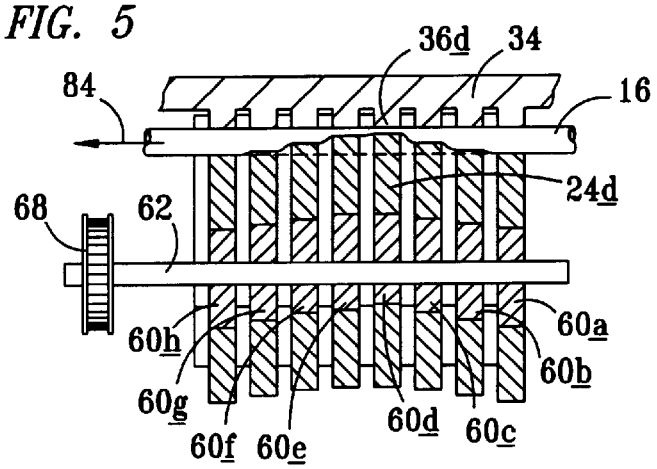
FIG. 5 is a partial schematic cross-sectional view taken along section lines 5—5 of FIG. 3 showing a plurality of sequentially actuated elements and reshaping fingers in which middle ones of the pumping elements are shown actuated to compress a flexible tubing and in which end ones of the interdigitated reshaping fingers are shown actuated to reshape the flexible tubing at points adjacent to retracted end pumping elements.

FIG. 3 shows a top plan view of pumping elements 24a, 24b, 24c, 24d, 24e, 24f and 24h and interdigitated reshaping fingers 26a through 26h. FIG. 5 shows a schematic cross-section taken in a side direction along a center line or a plane cut through the center of the pumping mechanism 20 with reshaping fingers, as shown in FIG. 3, along section line 5—5. In FIG. 5, it can be seen that the plurality of cams 60a through 60h each have an equal maximum eccentricity, which is shown in FIG. 5, with first cam 60a and last cam 60h both being offset in a maximum downward position in substantially equal amounts. The centrally located cam 60d is offset with its maximum eccentricity upward, completely compressing the IV tubing 16 against backing support bar 34, and in particular, against corresponding backing block 36d. As drive shaft 62 is rotated, each cam will be rotated against a corresponding pumping plate so that its maximum eccentricity completely closes the tubing 16. As the rotation continues, a wave-like action will pump fluid through IV tubing 16, as depicted with the flow direction arrow 84.

Also, as depicted in FIG. 3, when compression plate 24d is fully actuated to compress IV tubing 16, then IV tubing 16 will be flattened in a vertical direction so that it spreads outward in a horizontal direction. The cutout opening 30d is sufficiently wide to accommodate the horizontal spreading. It will also be seen that as compression plates 24a and 24h are both retracted downward in a vertical direction, IV tubing 16 tends to resiliently return to its original horizontal dimension. In order to facilitate the return of the tubing to its original shape, reshaping fingers 26a (which is correspondingly adjacent to pumping plate 24a) and reshaping fingers 26h (which is correspondingly adjacent to pumping plate 24h) are actuated inward as the pumping plate elements 24a and 24h retract.

Figure 4:
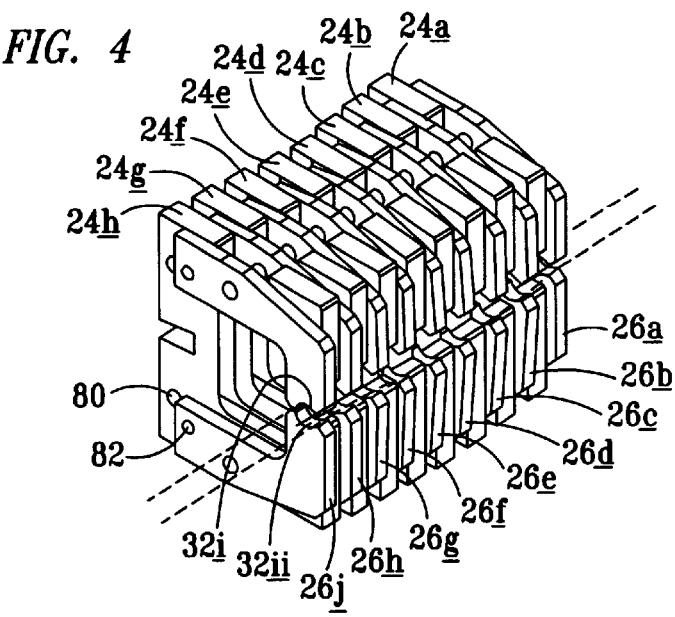
FIG. 4 is a schematic perspective view of a plurality of pumping element plates and a plurality of interdigitated reshaping fingers as in FIG. 3.

In the preferred embodiment, as shown in FIG. 2, there is at least one pair of reshaping fingers adjacent to each pumping plate. Most preferably, each end pumping element has two pairs of reshaping fingers, as shown in FIG. 4. In the embodiment of FIG. 4, additional reshaping fingers 26j are actuated simultaneously with fingers 26h by pumping element 24h. In this embodiment, the tubing on either side of each pumping element is reshaped. Each finger has a jaw 32 such that a pair of jaws 32i and 32ii are positioned in an opposed relationship. Jaws 32i and 32ii are automatically moved inward against the exterior walls of IV tubing 16. Jaws 32i and 32ii act in opposite directions for opposed reshaping contact. Thus, the IV tubing 16 which had previously been completely compressed (as shown at pumping plate 24d) becomes fully reshaped by adjacent reshaping pairs of reshaping jaws 32i and 32ii when the pumping plate 24 is actuated in a retracted or non-compression direction.

With reference to FIGS. 6, 7, 8 and 9, which depict a sequential series of pumping plate actuations and corresponding reshaping finger actuations. The pumping element compressions and releases, as well as the corresponding action of the reshaping fingers are depicted at four steps throughout an entire 360° rotation of cam drive shaft 62 for a single pumping element plate 24a and a corresponding pair of reshaping fingers 26ai and 26aii.

Figure 6:
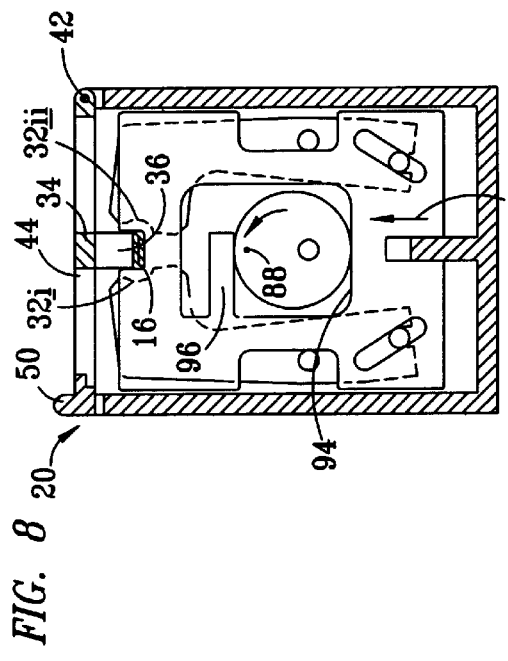
FIG. 6 is a schematic end view showing one pumping element plate in a retracted position so that the flexible tubing is opened at that point and showing the position of an adjacent pair of reshaping fingers (partially shown with hidden lines) engaged with the flexible tubing when it is released by the pumping element to reshape it to a circular cross-section, corresponding to an opened position in a pumping sequence.

With reference first to FIG. 6, the peristaltic pumping and reshaping mechanism 20 is shown encased within housing 22, which includes sidewalls 90 and 92. Pumping plate 24 is actuated in compression and release (or up and down, as shown in FIGS. 6–9). Edges 23 and 25 of each pumping plate 24 slide against the interior of walls 90 and 92, respectively. The lower portion of pumping plate 24 is guided in the preferred embodiment with a guide boss 86 which projects from a bottom 93 of housing 22, and which boss 86 is aligned with a groove 87 formed in pumping plate 24. Drive shaft 62 rotates the cams 60 (which rotation is schematically depicted with an arrow at a position indicated by a dot 88). Each cam 60 is positioned between a spring-loaded projection 96 and a cam following surface 94 of pumping plate 24, so that the pumping plate is reciprocated by the rotating eccentricity of cam 60. Pumping plates 24 are preferably constructed of a hard plastic material, such as nylon, and projections 96 are preferably formed integrally with the pumping plates 24. The resiliency of the nylon material causes each projection 96 to act as a spring-loaded cantilever. This preferred arrangement advantageously provides a direct drive between the cam 60 and the follower surface 94 when moving in a retracted pumping element direction. This is shown as a downward direction in FIGS. 6–9. Advantageously, when the cam 60 actuates the pumping plate 24 in a direction causing compression of tubing 16 against the backing block 36, there is a small amount of spring action available in projection 96 to prevent damage to the mechanism in the event of blockage. This spring action can accommodate manufacturing tolerances in the pump, as well as small differences in total tube wall thickness from one manufacturer to the next or in different manufacturing runs by the same tubing manufacturer.

In the preferred embodiment, the materials for manufacturing the pumping plates and the reshaping fingers are chosen for strength for lack of friction against each other and for chemical resistance. Advantageously, Delrin has been used for fingers, and nylon has been used for pumping elements. Other considerations of manufacturing may dictate the particulars of whether the fingers are Delrin and the pumping plates are nylon, or vice versa (i.e., nylon fingers and Delrin pumping plates). The object of reducing friction between the adjacent moving elements might also be accomplished by utilizing other materials according to this aspect of the disclosed invention.

Figure 7:
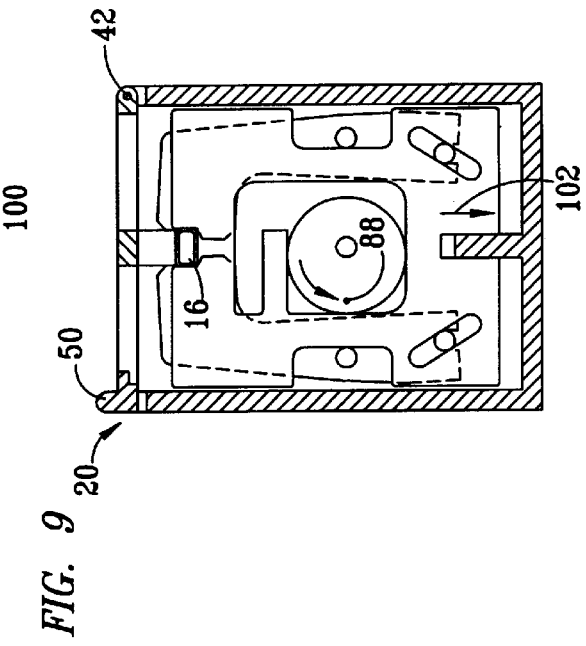
FIG. 7 is a schematic end view of the pumping element plate and adjacent pair of reshaping fingers of FIG. 6 shown in a subsequent partially compressed position in the pumping sequence.

Turning to FIG. 7, the cam 60 is shown to be moved to a position approximately 90° from the position depicted in FIG. 6. This is schematically indicated by the direction arrow and position indicator dot 88 move to the position, as shown in FIG. 7. Also, it can be seen that pumping element 24 is now moved upward with respect to the housing 22, as schematically indicated with vertical movement arrow 98. It will also be noted that in this position, tubing 16 becomes partially compressed because of the partial upward actuation and movement of pumping plate 24. Also, finger driving cam surfaces 80i and 80ii, which are formed in this embodiment as actuator channels 80i and 80ii, are moved with pumping plate 24 in an upward direction with respect to reshaping fingers 26i and 26ii. Cam followers 82i and 82ii are fastened to the fingers 26i and 26ii, respectively. Actuator channels 80i and 80ii are formed at an angle such that vertical movement between the actuator channels 80i and 80ii and the followers 82i and 82ii results in a horizontal component of movement to cam followers 82i and 82ii. The cam followers 82i and 82ii may be projections integrally formed on the reshaping fingers, or they may be pins projecting through the reshaping fingers. The reshaping fingers 26i and 26ii are pivotably mounted at axes 54 and 56, respectively, which provide pivot points located above the actuator channels 80 and follower 82. Thus, reshaping fingers 26i and 26ii pivot in opposite direction about pivot points 54 and 56, respectively, causing jaws 32i and 32ii on fingers 26i and 26ii to move outwardly, thereby accommodating the additional horizontal width of tubing 16 due to its partial compression by pumping plate 24.

Figure 8:
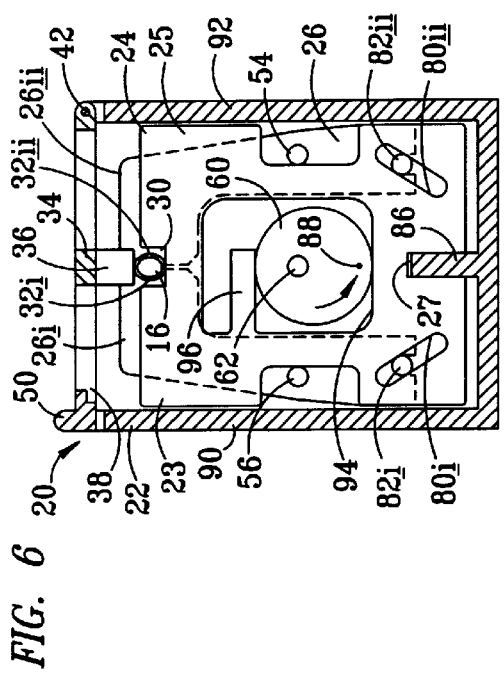
FIG. 8 is an end view of the pumping element plate and adjacent pair of reshaping fingers of FIGS. 6 and 7, shown with the pumping element in a fully compressed position during the pumping sequence so that the tubing is closed and the adjacent pair of reshaping fingers are completely retracted from the flexible tubing according to one embodiment of the present invention.

Referring now to FIG. 8, which is a depiction of the pumping and reshaping mechanism assembly 20 with shaft 62 and cam 60, shown rotated another 90°, as indicated with the arrow and position dot 88. Rotation of cam 60 will cause an additional amount of upward movement of element plate 24, as indicated with vertical movement arrow 100. As actuator channels 80i and 80ii are moved upward, cam followers 82i and 82ii will be pivoted inward about pivot rods 54 and 56 so that reshaping jaws 32i and 32ii at the top will be moved outward and will provide ample clearance for complete compression of IV tubing 16 to a closed and completely flattened condition.

Figure 9:
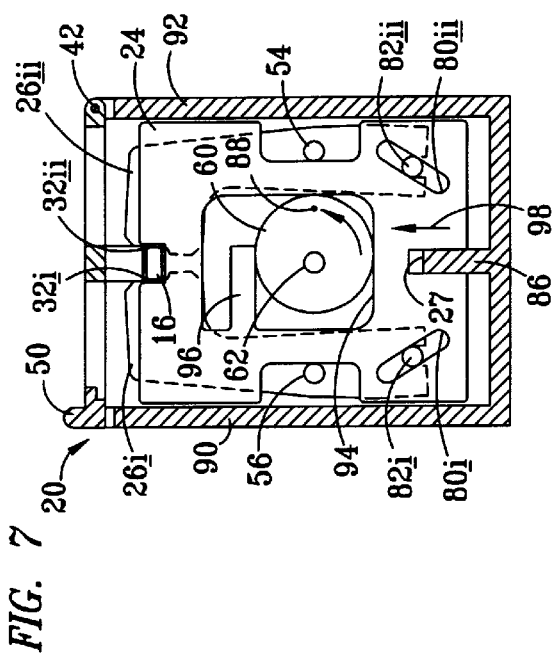
FIG. 9 is an end view of the pumping element plate and reshaping fingers of FIGS. 6, 7 and 8 shown with the pumping element in a partially retracted position and with the reshaping fingers shown partially actuated to engage with the flexible tubing for reshaping.

In FIG. 9, the peristaltic pumping mechanism 20 is shown with camshaft 62 having rotated cam 60 an additional 90°, as indicated by direction arrow and position dot 88. This will move pumping plate 24 downward, as indicated by motion arrow 102, so that tubing 16 again becomes partially opened. The relative motion between actuator channels 80i and 80ii and cam followers 82i and 82ii will act to pivot the reshaping fingers 26i and 26ii outward at the bottom and inward at the top, so that the reshaping jaws 32i and 32ii contact the previously compressed IV tubing 16 in opposed horizontal directions, thereby returning tubing 16 toward its original shape and an opened condition. Where the reshaping jaws 32i and 32ii are in the shape of concave arcs of a cylinder, with the same radius as the tubing 16, the tubing 16 will be reshaped to its original circular cross-sectional shape.

Reference again to FIG. 6 shows cam 60. The rotation direction arrow and position dot 88 indicate that cam 60 has been moved another 90°, thereby completing 360° of rotation, which moves pumping plate 24 to a full retracted position. This fully releases vertical compression from tubing 16. The relative motion between actuator channels 80*i* and 80*ii* with respect to followers 82*i* and 82*ii* acts to pivot reshaping fingers 26*i* and 26*ii* so that jaws 32*i* and 32*ii* fully engaged in opposed horizontal directions, thereby reshaping tubing 16 to its full circular cross-sectional condition.

Thus, it can be seen that due to the configuration and construction of the depicted embodiment of the invention, in which a plurality of reshaping finger pairs are interdigitated with the plurality of peristaltic pumping plates, the reshaping jaws 32*i* and 32*ii* can each be advantageously formed in the shape of an arcuate, concave surface which reshapes the tubing 16 to a substantially circular cross-section, thereby consistently returning it to its full volume at the point of reshaping jaw contact. Each jaw preferably contacts tubing 16 with an arc which is greater than about 90° so that more than about 180° of a circular shape results at total actuation of both reshaping jaws 32 against tubing 16. The reshaping contact occurs sequentially and alternately with the compression of the tubing. Throughout the operation of the peristaltic pumping mechanism 20, the tubing 16 is reshaped so that the interior volume of tubing 16, and thus the volumetric pumping rate for any given rotation speed of cam drive shaft 62, remains substantially constant throughout the operation of the peristaltic pumping and reshaping mechanism 20. Also, advantageously reshaping of the tubing 16 to its previous natural circular cross-sectional shape, without introducing new bends, reduces the introduction of new stresses and therefore reduces the fatigue to which tubing 16 is subjected, compared with reshaping as might be attempted without concave jaws. The useful life of a given portion of IV tubing is advantageously extended. In the case of a tubing 16, for example, this not only reduces costly monitoring and time-consuming replacement, but also it reduces potential for trauma to a patient due to or during IV replacement. Moreover, reshaping to a rounded shape facilitates accuracy by maintaining substantially the same return shape volume as with new tubing. The unique and unobvious interdigitated relationship between pumping plates 24 and reshaping fingers 26 advantageously allows the reshaping fingers 26 to be formed, having a concave, arcuate jaw shape, without interfering with the pumping elements themselves. Each jaw may be nearly semicircular so that complete reshaping is facilitated.

Turning now to FIGS. 10 through 13, an alternative embodiment of the invention is depicted, in which an alternative peristaltic pumping and reshaping mechanism 120 includes a housing 122 and sidewalls 190 and 192. There is a plurality of pumping plates 124 positioned therein along with a plurality of pairs of reshaping fingers 126. Each finger 126*i* and 126*ii* of the pair 126 has a corresponding reshaping jaws 132*i* and 132*ii*, respectively. The pumping element 124 is shown in the form of a pumping plate 124, which has angled finger driving cam surfaces 180*i* and 180*ii* formed thereon. Cam followers 182*i* and 182*ii* are attached to or formed on reshaping fingers 126*i* and 126*ii* and are slidingly held against the cam surfaces 180*i* and 180*ii*, respectively. The reshaping fingers 126 of this alternative embodiment are preferably constructed of a resilient plastic material, such as nylon, and are preferably formed to have arms 104*i* and 104*ii*, which are biased outward against sidewalls 190 and 192. The material of which the reshaping fingers 126*i* and 126*ii* are constructed is preferably resilient so that arms 104*i* and 104*ii* can be integrally formed with the reshaping fingers using cutout areas 106*i* and 106*ii*. This construction results in a spring-like action, when constructed of resilient material or which could be supplied by inserting a spring, such as a metallic coiled spring. This is schematically represented by depictions of springs at 108*i* and 108*ii*. Thus, cantilever projections or arms 104*i* and 104*ii* are "spring-loaded" against the inside walls 190 and 192. The spring tension, schematically depicted as 108*i* and 108*ii*, keeps the cam followers 182*i* and 182*ii* in constant contact with the respective finger driving cam surfaces 180*i* and 180*ii* of pumping element place 124.

Figure 10:
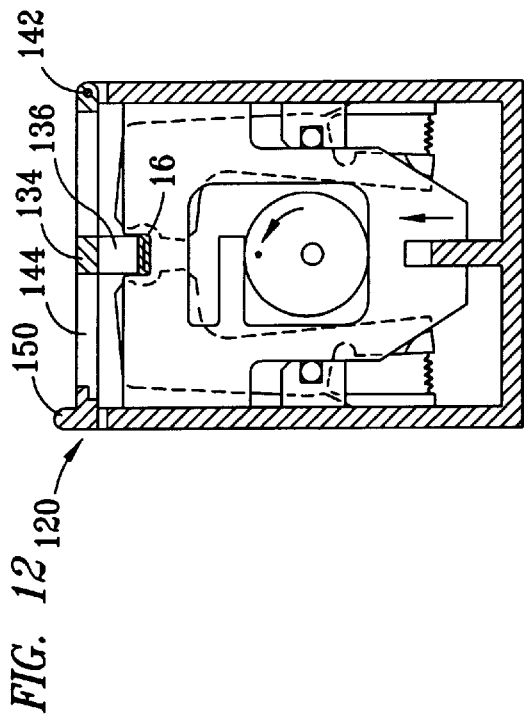
FIG. 10 is an end view of an alternative embodiment of a pumping element plate and reshaping fingers shown in a position in which said pumping element is retracted and said reshaping fingers are fully actuated into reshaping engagement with a flexible tubing.
Figure 11:
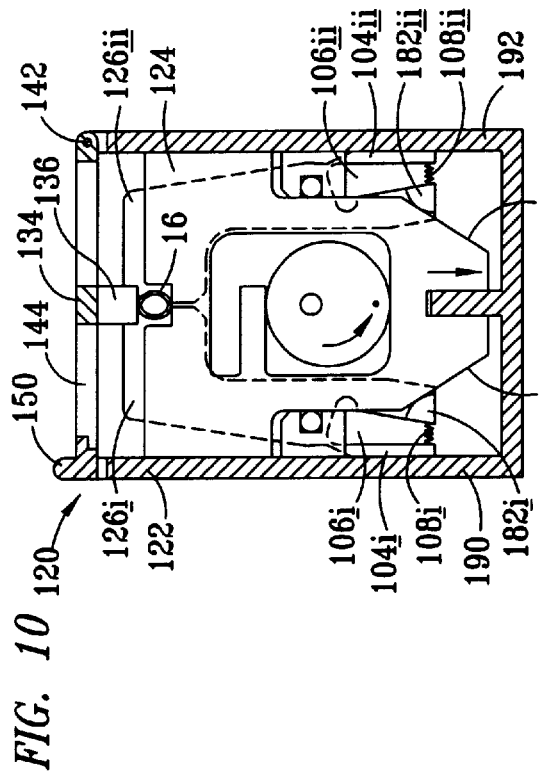
FIG. 11 is a end view of the pumping element and reshaping fingers of FIG. 10 shown in another sequential pumping position.

FIG. 11 depicts the peristaltic pump and reshaping assembly 120 of FIG. 10 in a position at which cam 160 is rotated 90° from the position shown in FIG. 10. In this position, tubing 16 is partially compressed, and cam followers 182*i* and 182*ii* are moved inwardly along angled cam surfaces 180*i* and 180*ii* due to the upward motion of pumping plate 124. The cutout openings 106*i* and 106*ii* are shown expanded slightly due to the resiliency of the material from which the reshaping fingers 126*i* and 126*ii* and arms 104*i* and 104*ii* are constructed, thereby providing the spring tension which is schematically depicted as 108*i* and 108*ii*. The motion of the cam followers inward at the bottom results in outward motion of concave reshaping jaws 132*i* and 132*ii* at the top. The operation is similar to that in the alternative embodiment previously depicted in FIGS. 6–9, except that the pumping plate 124 and the reshaping fingers 126*i* and 126*ii* are constructed differently, particularly in the area of the angled finger driving cam surfaces 180*i* and 180*ii* and the corresponding cam followers 182*i* and 182*ii* which are now provided with "spring loading" to maintain cam and follower contact.

Figure 12:
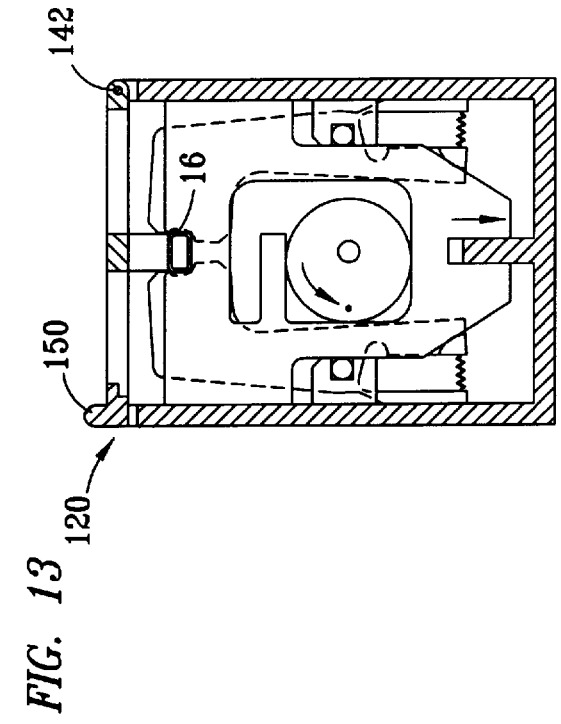
FIG. 12 is an end view of the pumping plate and reshaping fingers of FIGS. 10 and 11 shown in yet another pumping position; and, FIG. 13 is a end view of the pumping element plates of FIGS. 10, 11, and 12 shown in yet another sequential pumping position according to the present invention.

Referring to FIG. 12, the maximum upward motion of pumping element 124 is achieved with the cam 160 having its maximum eccentricity rotated to an upward position. Cam followers 182*i* and 182*ii* move along angled cam surfaces 180*i* and 180*ii* to their maximum inward position, thereby moving jaws 132*i* and 132*ii* to their maximum outward position so that any horizontal expansion of tubing 16 due to its compression to a completed closed condition is accommodated.

Figure 13:
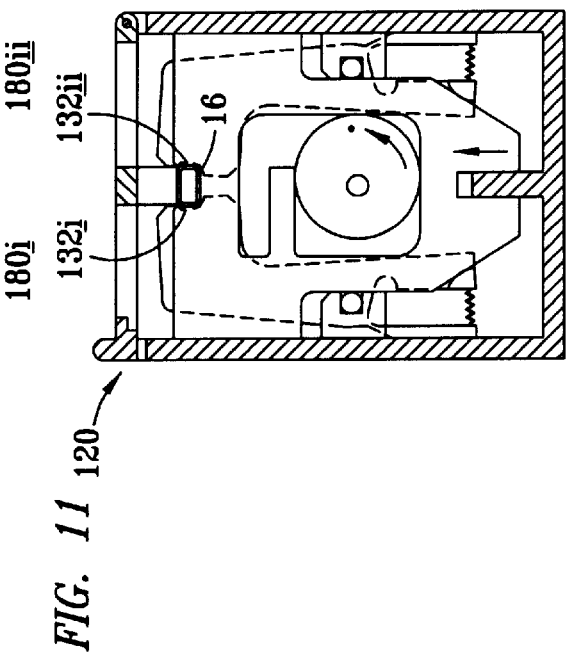

FIG. 13 depicts pumping element plate 124, partially retracted. The cam followers 182*i* and 182*ii* move along the cam surfaces 180*i* and 180*ii*, thereby causing the reshaping jaws 132*i* and 132*ii* to move inwardly, partially reshaping tubing 16. As with the embodiment depicted in FIGS. 6–10, reshaping is accomplished automatically as pumping plate 124 is withdrawn. The cycle is completed as shown in FIG. 10 in which tubing 16 is completely reshaped to its round, cross-sectional shape when the reshaping jaws 132*i* and 132*ii* move to their maximum inward position. The corresponding opposed jaws 132*i* and 132*ii* preferably define a substantially circular cross-section or cylindrical shape therebetween when pivoted fully inward. Reshaping of the flexible tubing 16 is completed immediately adjacent to each pumping contact point.

Figure 14:
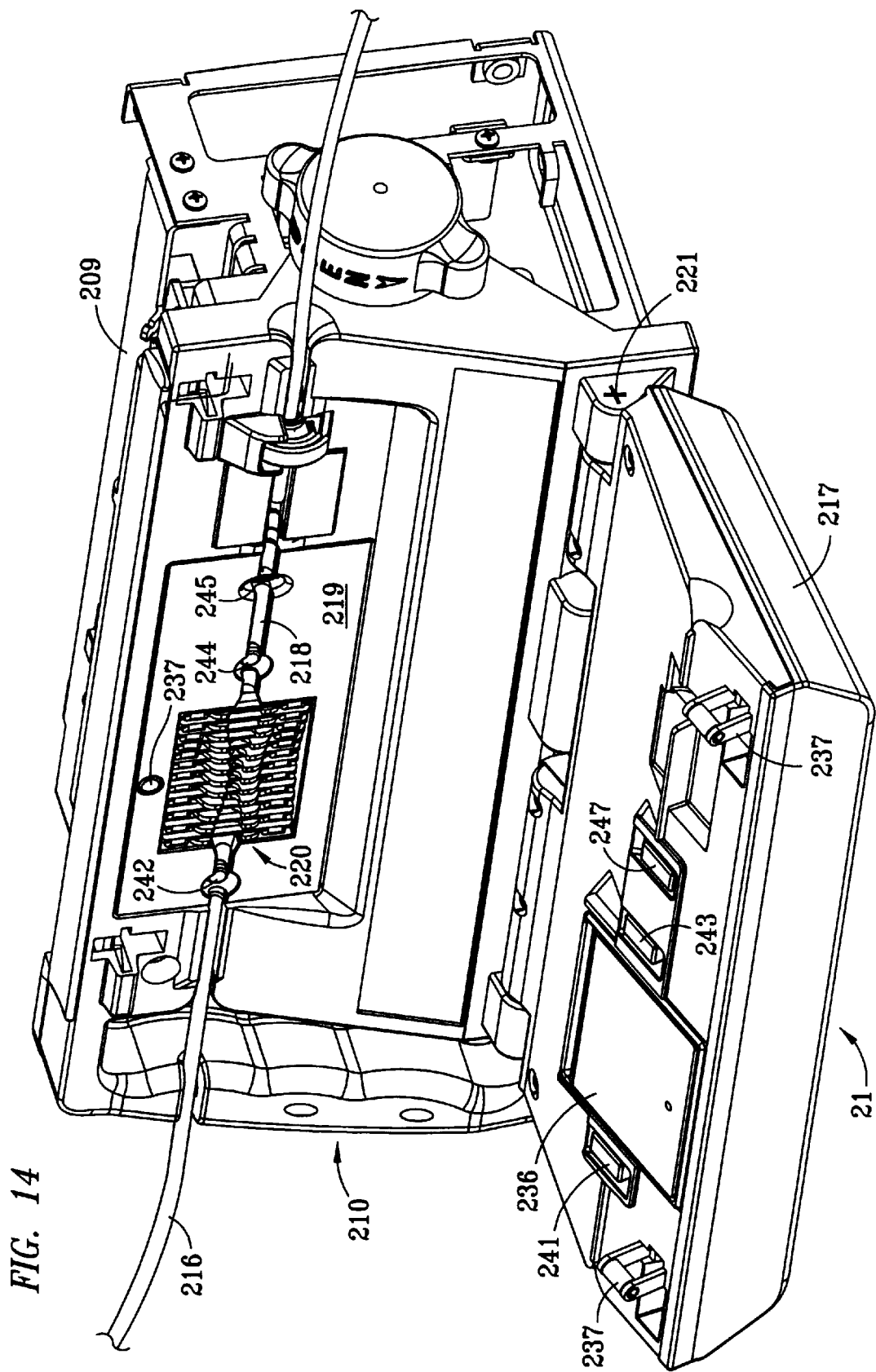
FIG. 14 is a perspective view of an alternative embodiment of a linear peristaltic pump.

Referring to FIG. 14 and alternative embodiment of a pump according to the present invention may be more fully understood. The pump 210 as depicted in the perspective view of FIG. 14 includes a pump body 209 having a door 217 pivotably attached as at hinges 221. A flexible tubing engagement pathway or channel 218 is formed along a face 219 of the pump 210. A pumping mechanism 220 that includes an assembly of pumping elements and reshaping fingers is mounted in the pump body 209 positioned along channel 218 for pumping and reshaping of a received flexible tubing 16. When door 217 is closed as by pivoting about hinges 221, a retractable spring loaded platen 236 is positioned against face 219 to provide a backing support surface for the pumping mechanism 220. Door 217 may be latched into a closed position using latches 237. Also positioned along the channel 218 on either side of the pumping mechanism 220 are upstream pressure sensor 242 and downstream pressure sensor 244. Also held in door 217 are spring loaded pressure supports including upstream pressure support 241 and downstream pressure support 243. According to the embodiment depicted in FIG. 14 there is also a downstream valve 245 and a correspondingly positioned spring loaded valve backing plate 247. The operation of the sensors and valve will be more fully discussed in reference to FIGS. 20–27 below.

Figure 15:
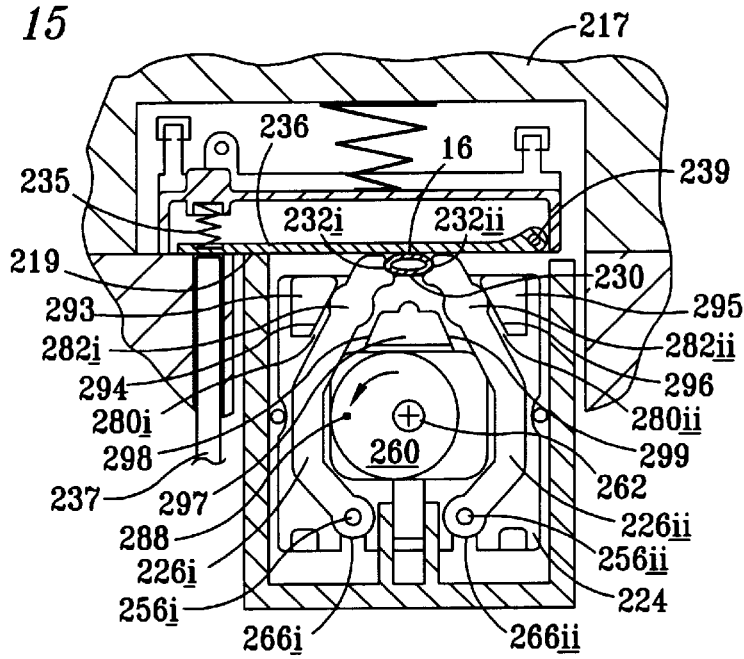
FIG. 15 is a schematic partial cross-sectional view through a portion of pump 10 with a door closed against a face of the pump body having a retractable platen spring loaded into a position for providing a backing surface to a pumping plate according to the invention.

FIG. 15 depicts a schematic partial cross-sectional view of pumping mechanism 220 in relation to the door 217 and retractable platen 236 and further depicting a pumping plate 224 and pairs of reshaping fingers 226i and 226ii according to the alternative embodiment of pump 210. The reciprocation position of the pumping plate 224 in FIG. 15 corresponds generally to the position in either of the alternative embodiments shown in FIGS. 9 or 13 above with pumping plate 224 moving downward due to rotation of cam 262. It can be seen that pumping plate 224 has a flat top surface 230 against which tubing 16 is compressed to pump fluid there through. Flat pumping surface 230 is parallel to the backing support surface provided by platen 236. The reshaping fingers 226i and 226ii are beginning to engage flexible tubing 16 with their respective reshaping jaws 232i and 232ii as pumping plate 224 retracts from flexible tubing 16. This motion is automatically accomplished using projection 293 having angled surface 294 and projection 295 having angled surface 296 formed on pumping plate 224. A third projection 297 centrally located on pumping plate 224 provides angled surface 298 and angled surface 299. The projections 293, 295 and 297 have approximately the same thickness as reshaping fingers 226i and 226ii and with their angled surfaces together form actuator channels 280i and 280ii which act against portions 282i and 282ii of reshaping fingers 226i and 226ii. Thus reshaping fingers 226i and 226ii are pivoted on pivot connector rods 256i and 256ii as the next adjacent pumping plate 224 reciprocates compressing and retracting in pumping action. Pumping plate 224 has slots 266i and 266ii formed to accommodate reciprocal motion relative to the connection pivot rods 256i and 256ii.

Figure 16:
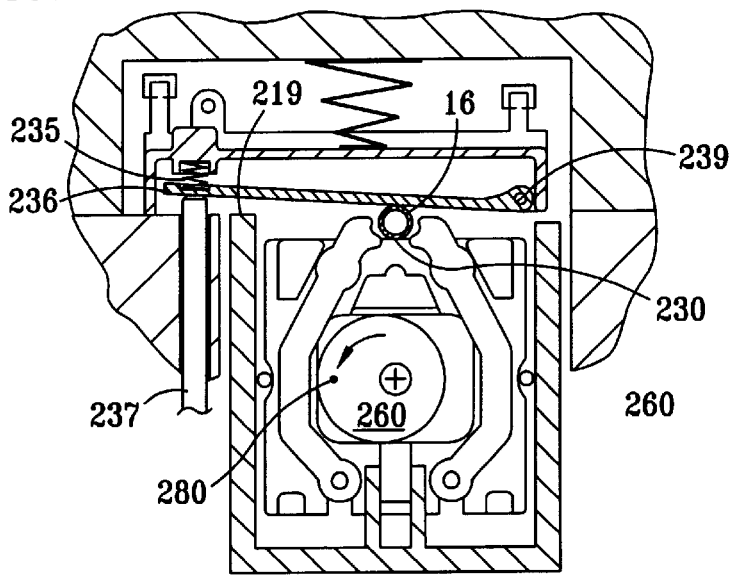
FIG. 16 is the mechanism of FIG. 15 with the platen shown retracted according to one aspect of the present invention.

FIG. 16 depicts schematic partial cross-sectional view similar to FIG. 15 showing retractable platen 236 in a position retracted against spring 235 through the actuation of retraction rod 237. The retraction rod 237 acts against one end of platen 236 with an opposite end of platen 236 pivotably connected at 239 to door 217. This lifts platen 236 off of flexible tubing 16. It is noted that platen 236 is raised off of tubing 16 regardless of the pumping position of cam 260 or any of the plurality of pumping plates 224. Platen 236 is raised a sufficient distance to allow flexible tubing 16 to become open through the resilience of flexible tubing 16.

Figure 17:
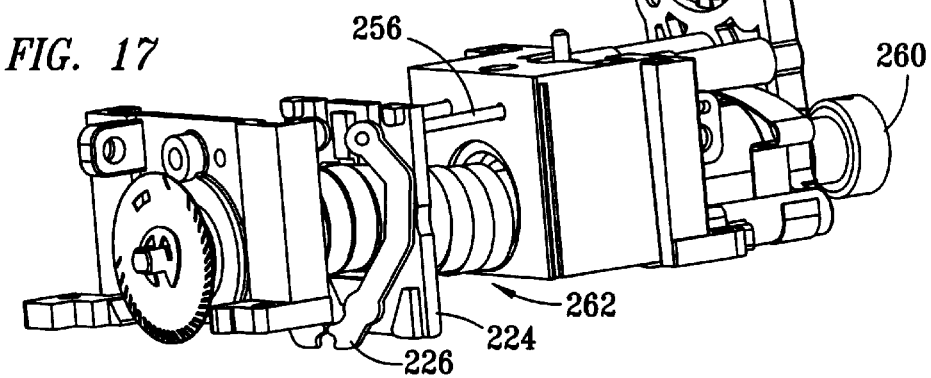
FIG. 17 is a partial schematic respective of a portion of the interior mechanism of the pump of FIG. 14 showing a representative one of the reshaping finger sets and an adjacent pumping plate engaged on the cam and camshaft assembly.

Other features of construction may be further understood with reference to the schematic prospective view in FIG. 17 of a portion of the pump 210 depicting a camshaft 260, a mount for motor 270 and schematically depicting only one of the plurality of pumping plates 224 and only one pair of the plurality of reshaping fingers 226 attached along connection rods 256i and 256ii. The remaining structure has been removed from view in FIG. 17 for clarity of understanding.

Figure 18:
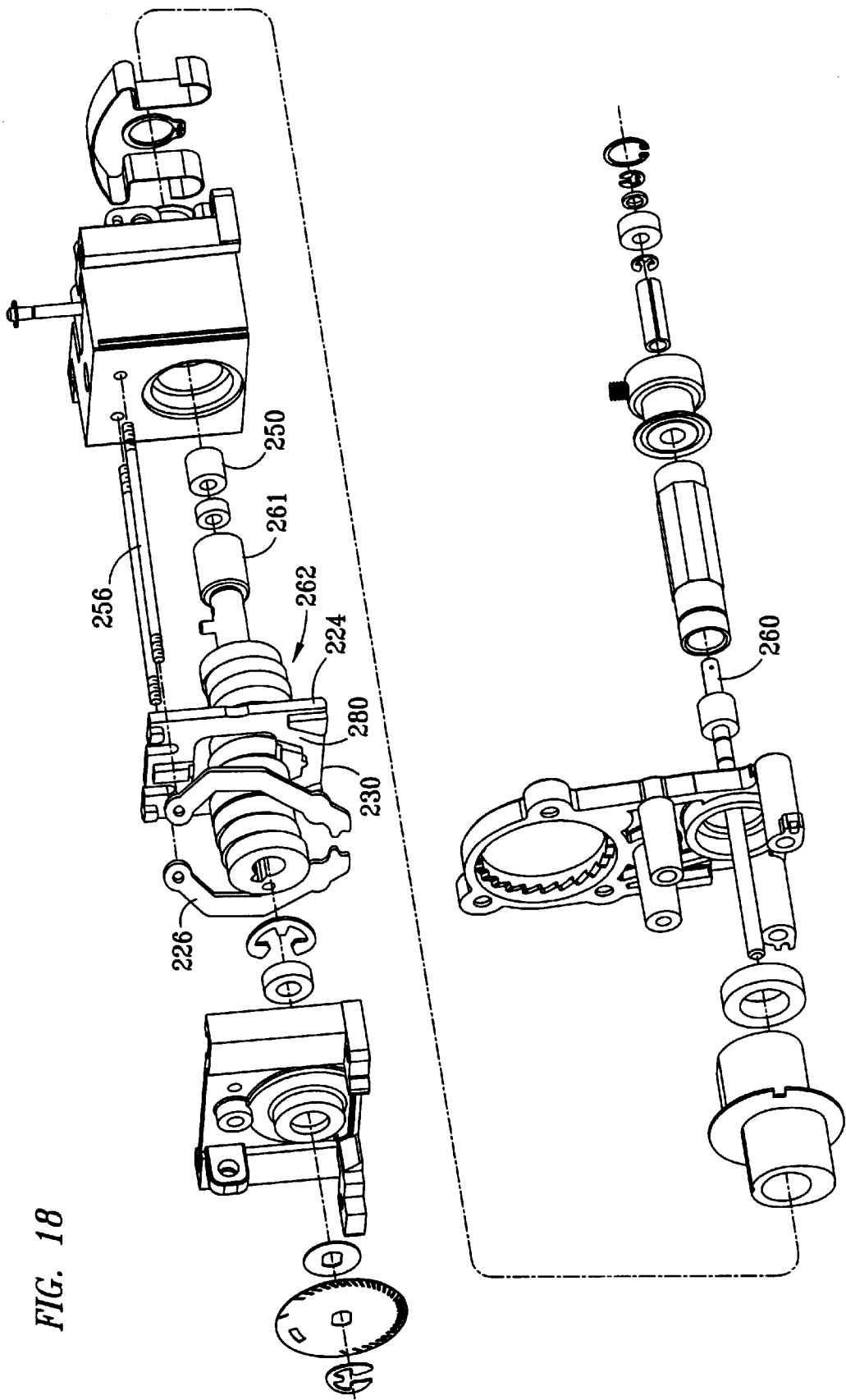
FIG. 18 is a schematic exploded assembly view of the portion of the mechanism of FIG. 17.

Further details of the structure according to FIG. 17 may also be understood with reference to FIG. 18. FIG. 18 is a schematic exploded assembly view of that portion of the pumping assembly 220 partially depicted in FIG. 17.

Figure 20:
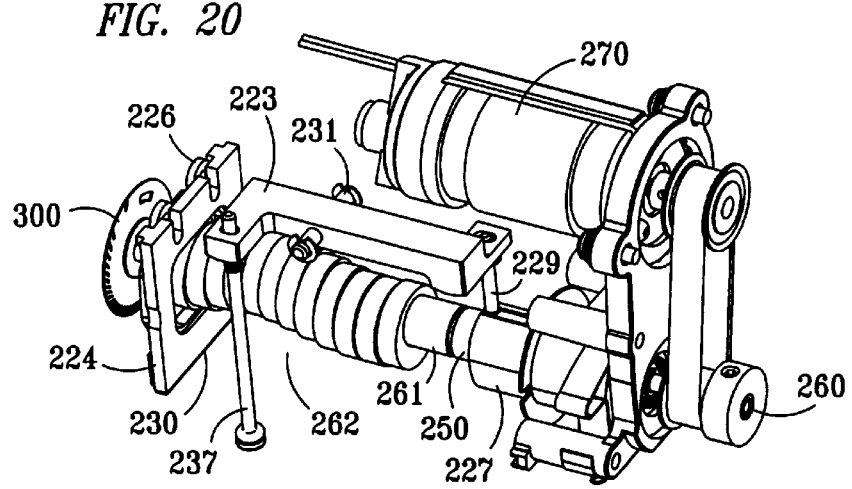
FIG. 20 depicts a schematic view of the camshaft motor and platen retraction mechanism removed from the structural body of schematic view of FIG. 19.

FIG. 20 schematically depicts the pumping camshaft 260 and the drive motor 270 as well as the actuating rod 237 and a platen lifting assembly according to the present invention for lifting the platen 236 (as shown previously in FIG. 16). The platen lifting rod 237 is connected to a lever 223 that pivots at 231 in response to a cam follower 229 actuated by a lift cam 227. Lift cam 227 is mounted through a one-way clutch assembly 250 to camshaft 260. Thus reverse rotation of motor 270 is required to engage clutch 250 and thereby rotate lift cam 227. Similarly cams 262 are mounted to cam 260 through a one-way clutch mechanism 261 that engages only in the forward motor rotation direction, (opposite direction from engagement of clutch 250). Thus reverse rotation to engages clutch 250 and disengages rotation of cams 262.

Figure 19:
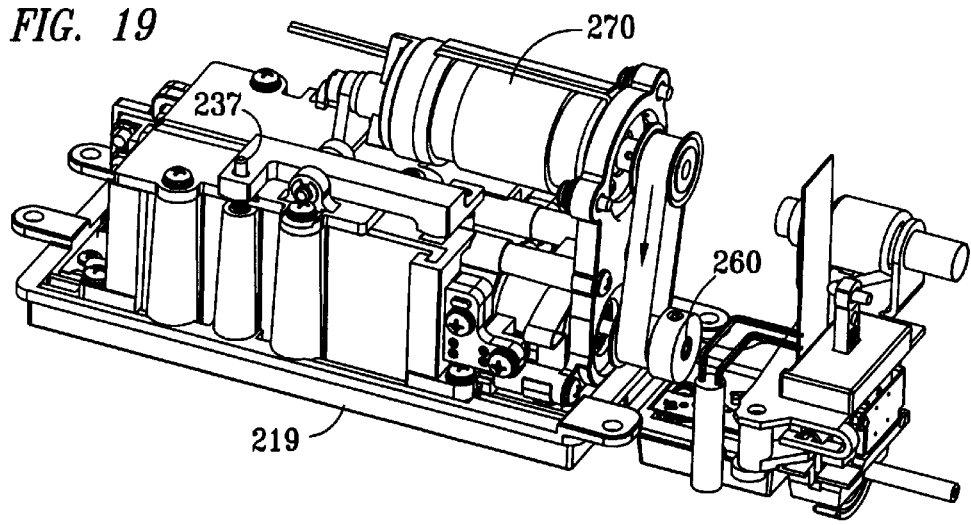
FIG. 19 is a schematic respective of an interior portion of the alternative embodiment of the pump in FIG. 14 depicting a drive motor coupled to a camshaft and a mechanism for retracting the platen that provides the backing plate to the pumping fingers according to the present invention.
Figure 21:
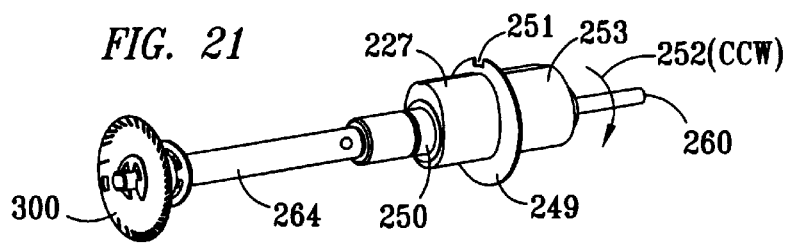
FIG. 21 is a schematic view of the camshaft in a first angular position depicting rotation of a portion of the shaft for initializing the operation of the pump so that the platen is appropriately retracted and the downstream valve is closed for equalization of pressure sensors according to one aspect of the present invention.

The purpose of retracting platen 236 is in part to initialize the pump sensors 242 and 244 as will be more fully understood with reference to FIG. 21. FIG. 21 is a schematic perspective depiction of the camshaft 260 with lifting cam 227 as well as lifting cam index wheel 249 and volume equalization timing wheel 300. For purposes of clarity of explanation the convention will be adopted herein to consider forward motor rotation as clockwise rotation viewing motor 270 from its driving end or from the right hand side of FIGS. 17, 19 and 20 and also from the right hand side viewing camshaft 260 from the right hand end as depicted in FIGS. 21,23,25 and 27 herein below. According to this convention the pumping cams 262 are driven with clockwise rotation of motor 270 and of camshaft 262 and the platen lifting cam 227 is driven with counterclockwise rotation of motor 270 and correspondingly camshaft 260. In FIG. 21 the rotation arrow depicts counterclockwise rotation. Preferably, when the pump is first started, and each time the door 217 is opened and then closed, an automatic initialization procedure is undertaken including counterclockwise rotation of cam 260, engaging clutch 250, and rotating cam 227 until the index notch 251 of index wheel 249 is in a proper position for raising cam follower 229 thereby actuating lever arm 233 to pivot lift actuator 237 against platen 236. In FIG. 21 counterclockwise rotation as a arrow 252 causes clutch 250 to engage cam 227. Counterclockwise rotation continues only until notch 251 of index wheel 249 is located at the proper platen liftoff position.

Figure 22:
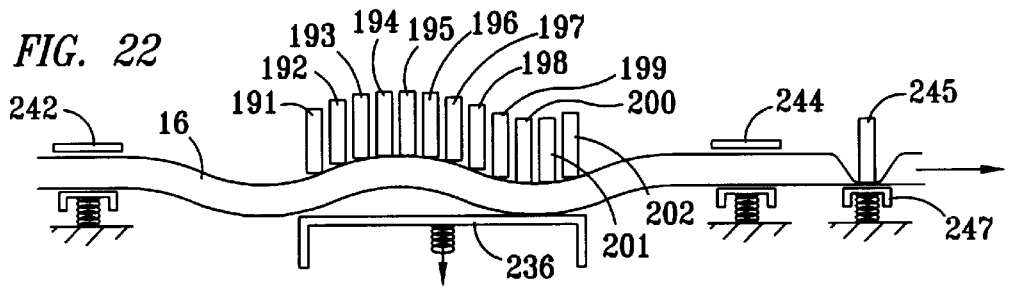
FIG. 22 is a schematic depiction of a flexible tubing received in the pump with the platen lifted and the downstream valve closed for initializing pumping operation.

FIG. 22 schematically depicts a lifted platen 236 so that tubing 16 is opened entirely along the pumping mechanism. The tubing 16 is released regardless of the position at which the operation was stopped. Thus for example as in FIG. 22 where the pumping plates 100 and 101 are in a down position so that tubing 16 would normally be closed if platen 236 was not lifted, the tubing 16 becomes opened as shown. With the platen 236 lifted, the valve 245 is also brought to a closed position pushing against spring loaded back plate 246. With the tubing 16 closed downstream from both pressure sensors 242 and 244 and with the tubing 16 opened therebetween the pressure inside of tubing 16 corresponds to the upstream pressure normally determined by the head height of a medical solution bottle or reservoir (not shown). Pressure sensors 242 and 244 may be constructed as strain gauge sensors such that the pressure inside of flexible tubing 16 corresponds to the expansion or contraction of tubing 16 relative to its normal size. With backing plates 241 and 243 against fixed surfaces on the face 219 of pump 210 the expansion of tubing 16 due to internal pressure may be accurately measured with sensors 242 and 244. By equalizing the pressure inside of tubing 16 at both the upstream pressure sensor 242 and at the downstream sensor 244 and without any pumping action taking place, the sensory input from 242 may be equalized with the sensory input of 244. Thus the operational relative pressure detected after the initial equalization will be accurately reflected both with respect to upstream sensor 242 and downstream sensor 244.

Figure 23:
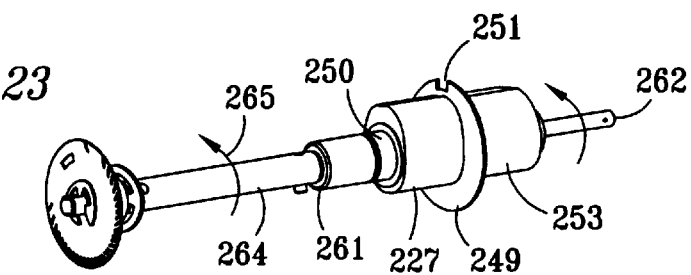
FIG. 23 is a schematic depiction of a camshaft rotated in a second step for initialization according to the present invention.
Figure 24:
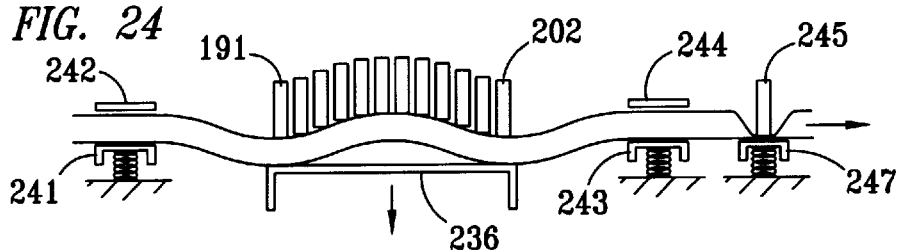
FIG. 24 is a schematic depiction of a received tubing corresponding to the cam rotation position depicted in FIG. 23.
Figure 25:
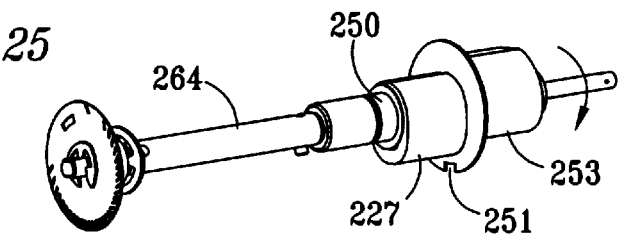
FIG. 25 is a schematic depiction of a further operational step in the initialization in which the platen is spring loaded against the face of the pump for providing the backing surface to the pumping fingers and into which the down stream valve is raised for allowing fluid flow.

Referring to FIG. 23 clockwise rotation 253 is initiated in camshaft 262 such that clutch 263 is engaged for clockwise rotation according to arrow 265, of a cam driver portion 264 of camshaft 262. Thus the cams 260 can be conveniently brought to their initialization position, as for example, referring also to FIG. 24 with both initial pumping plate 191 and terminal pumping plate 202 in a down or closed position. This initialization position can facilitate sensor equalization by causing the same relative flexure in tubing 16 relative to each upstream sensor 243 and to downstream sensor 244, thereby further facilitating accurate pressure measurements. To initialize pumping the motor 270 rotates again in a reverse or counterclockwise motion about 180 degrees of rotation so that platen lift cam 227 and downstream valve cam 253 both move to the opposite positions as shown in FIG. 25. This advances the platen 236 against tubing 16 so that platen 236 abuts by strong spring tension against face 217. Also downstream valve 245 is raised through the action of cam 253 so that tubing 16 is open and fluid pumping may begin.

Figure 26:
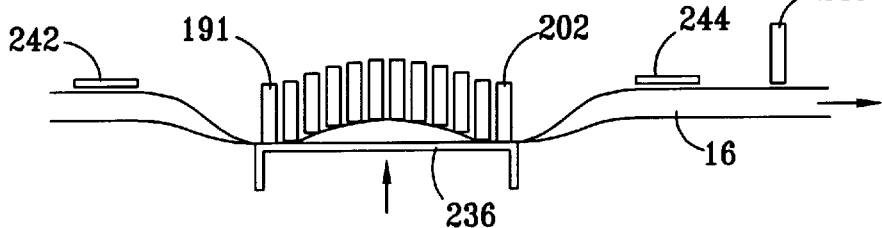
FIG. 26 is a schematic depiction of the pumping plates in the start position.

The start position depicted in FIG. 26 for the pumping plates also keeps the tubing 16 closed while valve 245 is raised.

Figure 27:
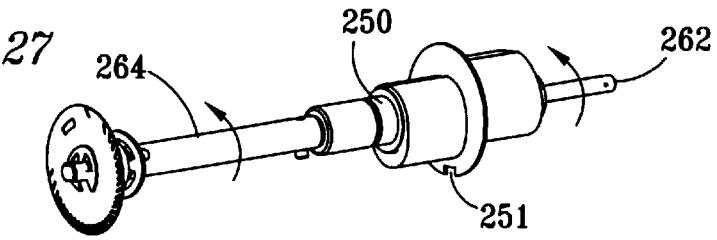
FIG. 27 is a schematic depiction of the camshaft of FIG. 25 at a beginning pumping rotation.

FIG. 27 depicts the start of operational pumping with camshaft 262 again rotated in a clockwise direction so that pump engaging portion 264 rotates in the clockwise direction 265 and operational fluid pumping begins.

Figure 28:
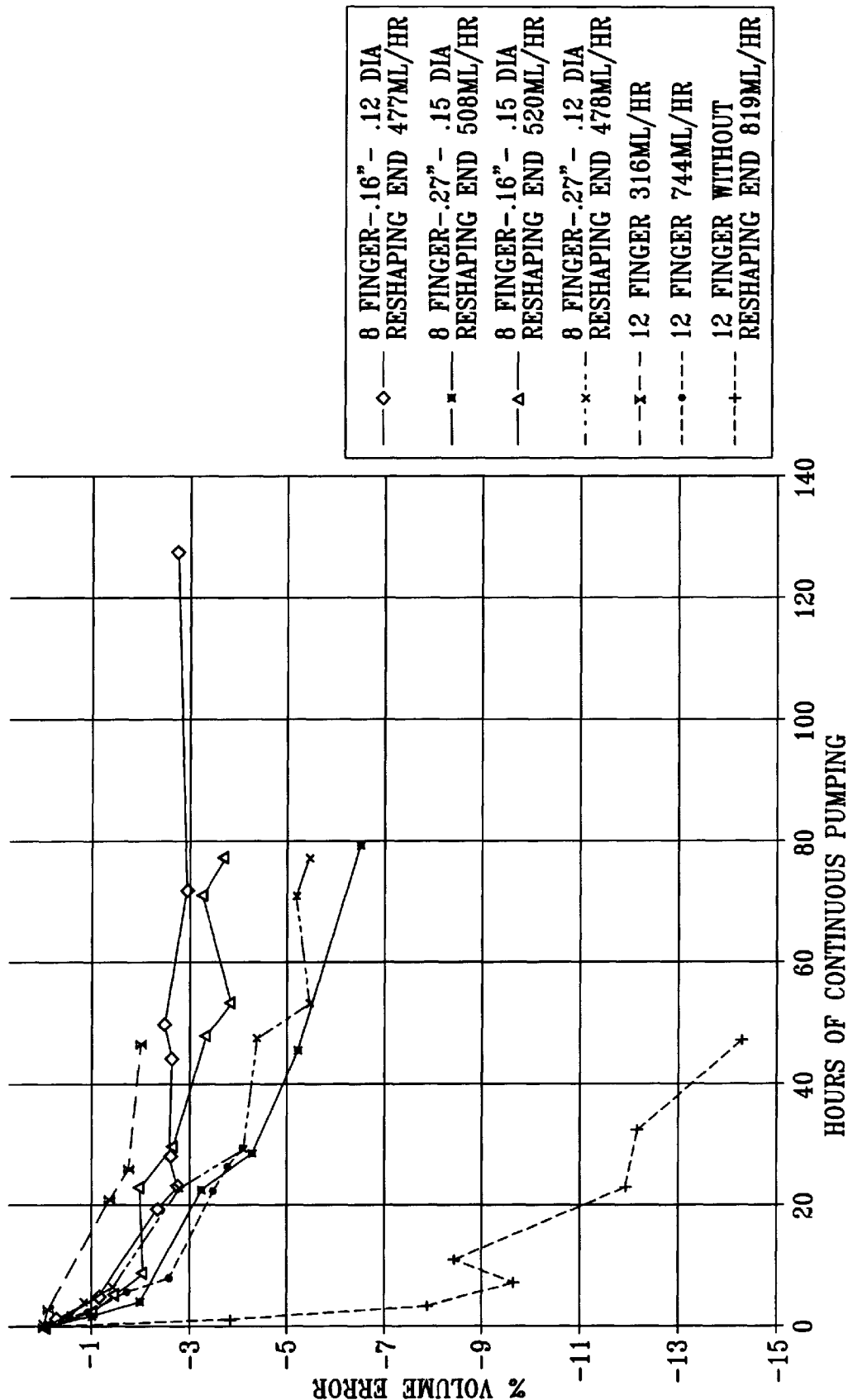
FIG. 28 is a graphical depiction of improved pumping accuracy obtained using a linear peristaltic pump according to the present invention.

FIG. 28 is a graphical depiction of improved pumping accuracy obtained using a linear peristaltic pump according to the present invention. FIG. 28 depicts the error percent from original volumetric output in a graphical depiction of hours. Line graphs of continuous pumping on the X axis compared to the percent volume error on the Y axis are presented for seven different configurations of a linear peristaltic pump according to the present invention, including a configuration with eight sets of reshaping fingers having 0.16" to 0.12" diameter reshaping ends operating at 477 ML/hour; a pump having eight reshaping fingers with 0.27" to 0.15" diameter reshaping end operating at 508 ML/hour; a pump with eight reshaping fingers having 0.16" to 0.15" diameter reshaping ends operating at 520 ML/hour; a pump with eight reshaping fingers having 0.27" to 0.12" diameter reshaping ends operating at 478 ML/hour; a pump having twelve reshaping finger sets operating at 316 ML/hour; a pump having twelve reshaping finger sets operating at 744 ML/hour; and a pump having twelve fingers without any reshaping ends operating at 819 ML/hour. The percent volume error or loss of volume is shown to be greater for the pump configuration without reshaping finger ends.

Other alterations and modifications and equivalents of the invention and its elements will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A linear peristaltic pump for use in pumping fluid through a flexible tubing and for reshaping said flexible tubing, comprising:

(a) a pump body, including a face having a channel formed therein for releasably receiving said flexible tubing into said channel and a door having a backing surface closable parallel to and against said face and against said flexible tubing received into said channel;

(b) a plurality of pumping elements operatively associated in said pump body for reciprocation therein, each of said pumping elements comprising plates having a tubing contact surface and a cam engaging surface, each said tubing contact surface of said plurality of pumping elements positioned for contact against said flexible tubing;

(c) a cam shaft having a plurality of cams for reciprocating each of said plurality of pumping elements sequentially between compression and release of said flexible tubing so that fluid is pumped through said flexible tubing;

(d) a plurality of reshaping fingers, each reshaping finger having first and second angled edge portions, each of said plurality of reshaping fingers pivotably mounted and positioned in said pump body so that said plurality of reshaping fingers are interdigitated with said plurality of pumping elements and positioned for non-collapsing reshaping contact with said flexible tubing adjacent to each of said plurality of pumping elements; and (e) first and second angled finger driving projections formed on each of said pumping elements defining actuator channels in which said reshaping fingers are movably engaged, said first angled finger driving projection for actuating each of said plurality of reshaping fingers sequentially into reshaping, non-collapsing contact against said flexible tubing, upon retraction of an adjacent one of said plurality of pumping elements corresponding to release of said tubing and said second finger driving projection for actuating each of said plurality of reshaping fingers sequentially out of reshaping contact upon advancement of said adjacent one of said plurality of pumping elements corresponding to compression of said tubing by adjacent ones of said plurality of pumping elements.

2. The linear peristaltic pump for use in pumping fluid through a flexible tubing and for reshaping said flexible tubing as in claim 1, wherein said tubing contact surface on each pumping plate defines a flat plane parallel to said face of said housing and extending coextensive with said pumping elements for pumping contact with said flexible tubing.

3. A linear peristaltic pump for pumping fluid through a flexible tubing, comprising:

(a) a pump body having a face with a channel elongated in a direction for receiving said flexible tubing thereinto;

(b) a plurality of pumping elements operatively associated in said pump body positioned along said channel for sequential reciprocation of each one of said pumping elements between compression and release of said flexible tubing;

(c) a drive mechanism operatively connected to said plurality of pumping elements through said pump body for driving said plurality of pumping elements with said sequential reciprocation;

(d) a plurality of separate reshaping fingers pivotably mounted and arranged in opposed a alternatingly interdigitated with said plurality of pumping elements and each reshaping finger positioned for pivoting into and out of non-collapsing reshaping contact with said flexible tubing and positioned adjacent to each of said plurality of pumping elements for sequentially reshaping said flexible tubing when sequentially released by each of said pumping elements;

(e) a plurality of finger driving cam mechanisms between said pumping elements and said reshaping fingers for sequentially actuating said reshaping fingers to pivot against said tubing upon release of said tubing by said each of said pumping elements; and (f) a retractable spring loaded platen mounted for spring loaded contact against said face of said pump to provide a substantially flat backing surface at a consistent position against which said pumping elements compress said flexible tubing.

4. A linear peristaltic pump as in claim 3 where:
(a) said drive mechanism comprises a variable speed electrical motor driving a rotary camshaft by which said pumping elements are reciprocated; and
(b) said controls operatively connected to said drive mechanism comprise a control panel having selectable input buttons for providing electrical signals to said variable speed motor to selectably change and thereby control the speed of said rotary camshaft.

5. An apparatus for pumping fluid through a flexible tubing as in claim 3 wherein a spring-loaded backing surface further comprises:
(a) a door pivotable into and out of a locked parallel position with and spaced apart from said tubing contact surfaces of said plurality of pumping plates;
(b) a platen held in said door for movement into and out of abutment against a face of said apparatus for pumping fluid and covering an area of pumping engagement with said flexible tubing;
(c) springs between said door and said platen to bias said platen into abutment with said face; and
(d) a retracting mechanism and controls for said retracted mechanism for selectably retracting said spring loaded platen out of abutment with said face for initializing said pump and for selectably releasing said spring loaded into abutment against said face for supporting said flexible tubing when it is sequentially compressed by said pumping plates during operation.

6. An apparatus for pumping fluid through a flexible tubing, comprising:
(a) a pump body having a face with a channel formed therein sized for removably receiving a fluid-filled flexible tubing and said pump body having a pump engagement portion along said channel;
(b) a door closable against said face of said pump body;
(c) a retractable spring-loaded backing surface formed in said door for contact with said face over said pump engagement portion;
(d) a plurality of pumping plates, each having a tubing contact surface and each mounted along said pump engagement portion in said pump body adjacent each other one of said plurality of pumping plates for reciprocating motion compressing against and retracting from said flexible tubing when said door is closed and when said flexible tubing is engaged between said contact surfaces of said plurality of pumping plates and said retractable spring loaded backing surface;
(e) a plurality of rotary cams for reciprocating said plurality of pumping plates sequentially so that fluid is movable through said flexible tubing by action of said reciprocating pumping plates;
(f) a plurality of reshaping fingers, each separately and pivotably mounted in said pump body interdigitated with said plurality of pumping plates, said reshaping fingers constructed and positioned for non-collapsing transverse reshaping contact with said flexible tubing, each reshaping finger positioned for contacting said flexible tubing adjacent to at least one of said pumping plates;

(g) angled finger driving projections formed on each of said pumping plates for moving each of said reshaping fingers out of contact with said tubing when said adjacent one of said plurality of pumping plates is compressed against said tubing and for advancing each of said reshaping fingers into non-collapsing reshaping contact with said flexible tubing when said adjacent one of said plurality of pumping plates is retracted from said flexible tubing;

(h) an upstream pressure sensor in said face of said pump body along said channel upstream from said pump engagement portion;

(i) a downstream pressure sensor in said face of said pump along said channel downstream from said pump engagement portion;

(j) a valve positioned along said channel downstream from said downstream sensor said valve actuatable to close said flexible tubing when received in said channel and retractable to open said flexible tubing during operation of said apparatus for pumping; and (k) a retraction mechanism for retracting said spring loaded backing surface from said face of said pump body when said valve downstream from said downstream sensor is actuated to close said flexible tubing so that said downstream and upstream sensors can be calibrated at the same internal fluid pressure.

7. An apparatus for pumping fluid through a flexible tubing comprising:
(a) a pump body having a face with a channel formed therein sized for removably receiving a fluid-filled flexible tubing and said pump body having a pump engagement portion along said channel;
(b) a door closable against said face of said pump body;
(c) a retractable spring loaded backing surface formed in said door for contact with said face over said pump engagement portion;
(d) a plurality of pumping plates, each having a tubing contact surface and each mounted along said pump engagement portion in said pump body adjacent each other one of said plurality of pumping plates for reciprocating motion compressing against and retracting from said flexible tubing when said door is closed and when said flexible tubing is engaged between said contact surfaces of said plurality of pumping plates and said retractable spring loaded backing surface;
(e) a plurality of rotary cams for reciprocating said plurality of pumping plates sequentially so that fluid is movable through said flexible tubing by action of said reciprocating pumping plates;
(f) a plurality of reshaping fingers, each separately and pivotably mounted in said pump body interdigitated with said plurality of pumping plates, said reshaping fingers constructed and positioned for non-collapsing transverse reshaping contact with said flexible tubing, each reshaping finger positioned for contacting said flexible tubing adjacent to at least one of said pumping plates;
(g) angled finger driving projections formed on each of said pumping plates for moving each of said reshaping fingers out of contact with said tubing when said adjacent one of said plurality of pumping plates is compressed against said tubing and for advancing each of said reshaping fingers into non-collapsing reshaping contact with said flexible tubing when said adjacent one of said plurality of pumping plates is retracted from said flexible tubing;

(h) an upstream pressure sensor in said face of said pump body along said channel upstream from said pump engagement portion;

(i) a downstream pressure sensor in said face of said pump along said channel downstream from said pump engagement portion;

(j) a valve positioned along said channel downstream from said downstream sensor said valve actuatable to close said flexible tubing when received in said channel and retractable to open said flexible tubing during operation of said apparatus for pumping;

(k) a retraction mechanism for retracting said spring loaded backing surface from said face of said pump body when said valve downstream from said downstream sensor is actuated to close said flexible tubing so that said downstream and upstream sensors can be calibrated at the same internal fluid pressure; and (l) a second spring loaded backing plate on said door adjacent to said downstream valve so that said second backing surface contacts said face of said pump when said door is closed thereby maintaining the face of said pump as a reference surface for said valve actuation.

8. The apparatus for pumping fluid of claim 6 further comprising a third and fourth spring loaded backing plates on said door adjacent to said upstream and said downstream pressure sensors for contacting said face of said housing when said door is closed so that said face is maintained as a reference surface for said pressure sensors.

9. A method of pumping fluid through a flexible tubing and of reshaping said tubing during said pumping, comprising the steps of:

(a) releasably engaging said flexible tubing into a channel of predetermined depth formed in a face of a linear peristaltic pump along a plurality of pumping element for pumping fluid through said tubing;

(b) applying a spring loaded backing plate against said face and said flexible tubing engaged into said channel in said face;

(c) reciprocating each of said plurality of pumping elements sequentially between compression and release of said flexible tubing against said backing plate along a length of said tubing thereof so that fluid is pumped there through;

(d) actuating each of a plurality of reshaping fingers sequentially with non-collapsing reshaping contact against said tubing, corresponding to release thereof by adjacent ones of said plurality of pumping elements; and (e) initializing said apparatus for pumping fluid by retracting said spring loaded backing plate from said engaged flexible tubing, sensing pressure in said flexible tubing, with separate upstream and downstream sensors, when said backing plate is retracted and said tubing is released, normalizing the upstream and downstream pressure sensed by said separate sensors and placing said backing plate into spring loaded contact with said pump face into which said flexible tubing is engaged so that said pumping elements actuate against said tubing at a precise position determined by said depth of said channel.

* * * * *

UNITED STATES PATENT AND TRADEMARK OFFICE
CERTIFICATE OF CORRECTION

PATENT NO. : 6,234,773 B1
DATED : May 22, 2001
INVENTOR(S) : Roger J. Hill; James H. Monti, Jr.; Joseph A. Oliver; Gary Lindemann; Harry C. Copp It is certified that error appears in the above-identified patent and that said Letters Patent is hereby corrected as shown below:

<u>Column 16,</u>
Line 62, "in opposed a alternatively" should be -- in opposed pairs alternatively --.

Signed and Sealed this

Eighth Day of January, 2002

*Attest:*

*Attesting Officer*

JAMES E. ROGAN
*Director of the United States Patent and Trademark Office*